United States Patent
Sanada et al.

(10) Patent No.: US 8,440,589 B2
(45) Date of Patent: May 14, 2013

(54) AZOMETHINE COMPOUND AND THERMAL TRANSFER SHEET USING COLORING MATTER OF THE AZOMETHINE COMPOUND

(75) Inventors: Tomoyuki Sanada, Okayama (JP); Tsuaki Odaka, Okayama (JP); Hiroyuki Hasegawa, Okayama (JP); Hiroko Amano, Suginami-Ku (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 254 days.

(21) Appl. No.: 13/056,205

(22) PCT Filed: Mar. 31, 2010

(86) PCT No.: PCT/JP2010/055903
§ 371 (c)(1),
(2), (4) Date: Jan. 27, 2011

(87) PCT Pub. No.: WO2010/114038
PCT Pub. Date: Oct. 7, 2010

(65) Prior Publication Data
US 2011/0129624 A1    Jun. 2, 2011

(30) Foreign Application Priority Data

Mar. 31, 2009 (JP) ................. 2009-085637
Mar. 31, 2009 (JP) ................. 2009-087269

(51) Int. Cl.
*B41M 5/39* (2006.01)
*C09B 55/04* (2006.01)

(52) U.S. Cl.
USPC .......................... 503/227; 534/769

(58) Field of Classification Search ........... None
See application file for complete search history.

(56) References Cited

U.S. PATENT DOCUMENTS

| | | |
|---|---|---|
| 5,476,943 A | 12/1995 | Komamura et al. |
| 5,612,282 A | 3/1997 | Komamura et al. |
| 5,753,017 A | 5/1998 | Onodera et al. |

FOREIGN PATENT DOCUMENTS

| | | |
|---|---|---|
| EP | 0 616 898 A2 | 9/1994 |
| JP | 05-239367 A1 | 9/1993 |
| JP | 07-166084 A1 | 6/1995 |
| JP | 09-111163 A1 | 4/1997 |
| JP | 2840901 B2 | 12/1998 |
| JP | 3013137 B2 | 2/2000 |
| JP | 3078308 B2 | 8/2000 |
| JP | 2008-087309 A1 | 4/2008 |
| JP | 2009-227774 A1 | 10/2009 |

OTHER PUBLICATIONS

Extended European Search Report dated Aug. 23, 2012.
Chinese Office Action dated Jan. 6, 2013 (with English translation).

*Primary Examiner* — Bruce H Hess
(74) *Attorney, Agent, or Firm* — Burr & Brown

(57) ABSTRACT

This invention provides an azomethine compound that can realize a good coupling reaction and, at the same time, can significantly reduce the production cost of the azomethine compound, the azomethine compound comprising a pyridine ring bonded through a nitrogen atom to a 1H-pyrazolo[1,5-b][1,2,4]triazole ring. The azomethine compound is represented by formula (M-I):

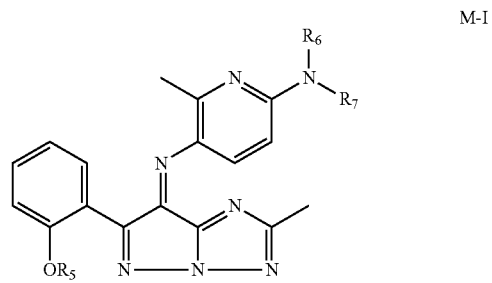

M-I wherein $R_1$ represents a phenyl group or a naphthyl group optionally substituted by an alkyl group or a halogen; and $R_2$ and $R_3$ each independently represent a C2-4 (number of carbon atoms) alkyl group.

12 Claims, No Drawings

AZOMETHINE COMPOUND AND THERMAL TRANSFER SHEET USING COLORING MATTER OF THE AZOMETHINE COMPOUND

FIELD OF INVENTION

The present invention relates to a novel azomethine compound, and more specifically relates to a novel azomethine compound which has high lightfastness, can be produced at low cost, and can realize excellent color tones when the compound is used as a magenta coloring matter, and a thermal transfer sheet using a coloring matter, for thermal dye transfer recording, comprising the novel azomethine compound.

BACKGROUND ART

A dye sublimation thermal transfer method (a thermal sublimation-type transfer method) is a method that comprises providing a thermal transfer film comprising a base material bearing a dye layer on its surface, the dye layer having been formed using a solution or dispersion of a sublimable dye in a binder resin, superimposing the thermal transfer film on an image receiving film, applying energy according to image information to a heating device such as a thermal head to transfer the sublimable dye, contained in the dye layer in the thermal transfer film, onto the image receiving film and thus to form an image.

The thermal sublimation-type transfer method is advantageous, for example, in that, since the amount of the dye to be transferred can be regulated dot by dot by regulating the amount of energy applied to the thermal transfer film, excellent gradational images can be formed and, at the same time, characters, symbols and the like can simply be formed.

In this thermal transfer method, high-quality images comparable with silver salt photographs can be formed. This has led to a very strong demand for the prevention of a deterioration in the quality of images due to factors such as light, heat and humidity, and, in order to satisfy this demand, the development of various sublimable dyes for image storage stability improvement purposes has been made.

For example, Japanese Patent No. 3013137 (patent document 1) and Japanese Patent No. 3078308 (patent document 2) disclose, as a coloring matter, for thermal dye transfer recording, possessing excellent transferability and storage stability, an azomethine compound having a structure comprising a 1H-pyrazolo[5,1-C][1,2,4]triazole ring as a coupler and a pyridyl group bonded to the coupler through a nitrogen atom. Further, Japanese Patent No. 2840901 (patent document 3) discloses an azomethine compound having a structure comprising a 1H-pyrazolo[1,5-b][1,2,4]triazole ring as a coupler and a phenylamino group bonded to the coupler through a nitrogen atom. Furthermore, Japanese Patent Application Laid-Open No. 239367/1993 (patent document 4) discloses an azomethine compound having a structure, which is a combination of both the above structures, comprising a pyridyl group bonded to a 1H-pyrazolo[1,5-b][1,2,4]triazole ring coupler through a nitrogen atom.

The azomethine coloring matters disclosed in Japanese Patent No. 3013137 and Japanese Patent No. 3078308 have high lightfastenss but pose a problem of cost because the 1H-pyrazolo[5,1-C][1,2,4]triazole ring functions as the coupler. Further, the azomethine coloring matter, which is described in Japanese Patent No. 2840901 and uses the 1H-pyrazolo[1,5-b][1,2,4]triazole ring compound as the starting material coupler, can be advantageously produced at relatively low cost but sometimes suffers from unsatisfactory lightfastness.

On the other hand, the coloring matter, which is described in Japanese Patent Application Laid-Open No. 239367/1993 and comprises a combination of the 1H-pyrazolo[1,5-b][1,2,4]triazole ring coupler with the pyridyl group, can be advantageously produced at low cost and, at the same time, has high lightfastness. In particular, compounds 9, 10, 11, 22, and 112, which are proposed in Japanese Patent Application Laid-Open No. 239367/1993 and have a phenyl group introduced as substituent $R_6$ of the 1H-pyrazolo[1,5-b][1,2,4]triazole ring, are advantageous in that the color tone of the coloring matter is close to a required color reproduction region. Compounds described in Japanese Patent Application Laid-Open No. 239367/1993, especially compounds with an unsubstituted pyridyl group introduced thereinto as substituent $R_6$ of the triazole ring, are advantageous in production cost and lightfastness but suffer from a low degree of conversion in the coupling reaction and provide a yield of about 20% as described also in Japanese Patent Application Laid-Open No. 239367/1993.

Further, in addition to the development of yellow, magenta, and cyan dyes, various research and development have also been made on a combination of dyes of these colors. For example, Japanese Patent Application Laid-Open No. 87309/2008 (patent document 5) proposes a thermal transfer sheet that can yield printed matters having various excellent fastness properties such as high lightfastness and less susceptibility to catalytic fading through a combination of specific yellow dye coloring matter, magenta dye coloring matter, and cyan dye coloring matter.

PRIOR ART DOCUMENTS

[Patent document 1] Japanese Patent No. 3013137
[Patent document 2] Japanese Patent No. 3078308
[Patent document 3] Japanese Patent No. 2840901
[Patent document 4] Japanese Patent Application Laid-Open No. 239367/1993
[Patent document 5] Japanese Patent Application Laid-Open No. 87309/2008

SUMMARY OF THE INVENTION

Problems to be Solved by the Invention

The present inventors have now found that azomethine compounds, which comprise a pyridine ring bonded to a 1H-pyrazolo[1,5-b][1,2,4]triazole ring through a nitrogen atom and have a specific substituent, have excellent lightfastness and production cost and, at the same time, can realize high yield and excellent dissolvability and sensitivity as a coloring matter. The present, inventors have further found that a combination of a specific yellow dye coloring matter, a magenta dye coloring matter containing the above azomethine compound, and a cyan dye coloring matter can suppress catalytic fading to a certain extent and can improve lightfastness of a mixed color, especially black which is a tertiary color. The present invention has been made based on such finding.

Accordingly, an object of the present invention is to provide a novel azomethine compound that has excellent lightfastness and production cost and, at the same time, can realize high yield and excellent dissolvability and sensitivity as a coloring matter.

Another object of the present invention is to provide a thermal transfer sheet that comprises a combination of a specific yellow dye coloring matter, a magenta dye coloring matter containing the above azomethine compound, and a cyan dye coloring matter and can realize excellent lightfastness of a mixed color, especially black which is a tertiary color.

Means for Solving the Problems

According to the present invention, there is provided an azomethine compound represened by formula M-I:

[Chemical formula 1]

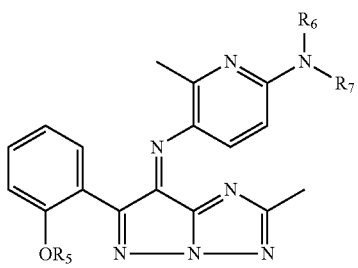

M-I wherein $R_5$ represents a C1-3 (number of carbon atoms) straight chain or branched chain alkyl group; and $R_6$ and $R_7$ each independently represent a C2-4 (number of carbon atoms) alkyl group.

According to another aspect of the present invention, there is provided a thermal transfer sheet comprising at least a yellow dye layer, a magenta dye layer, and a cyan dye layer, the yellow dye layer, the magenta dye layer, and the cyan dye layer each comprising a base material and a dye layer that contains a dye coloring matter and a binder resin and is provided on the base material, the yellow dye comprising a dye coloring matter represented by formulae Y-I and/or Y-II:

[Chemical formula 2]

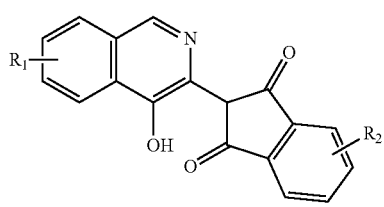

Y-I wherein $R_1$ represents an alkyl group, an aryl group, a hydrogen atom, or a halogen atom; and $R_2$ represents a carbonylamino group or a carbonylalkoxy group:

[Chemical formula 3]

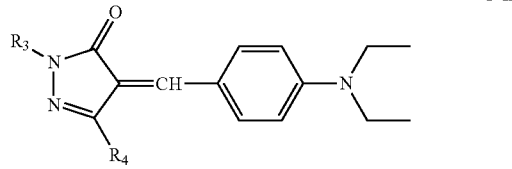

Y-II wherein $R_3$ represents an alkyl group, an aryl group, or a hydrogen atom; and $R_4$ represents an alkyloxy group, an aryloxy group, or an amino group, the magenta dye comprising a dye coloring matter represented by formula M-I:

[Chemical formula 4]

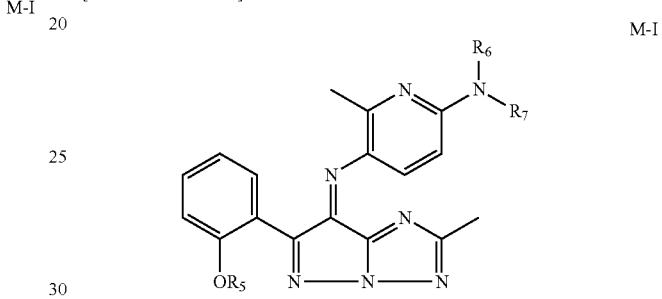

M-I wherein $R_5$ represents a C1-3 (number of carbon atoms) straight chain or branched chain alkyl group; and $R_6$ and $R_7$ each independently represent a C2-4 (number of carbon atoms) alkyl group, the cyan dye comprising a dye coloring matter represented by formula C-I:

[Chemical formula 5]

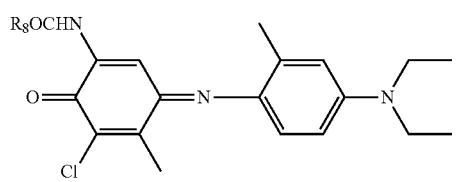

C-I wherein $R_8$ represents an alkyl group or an aryl group.

Effect of the Invention

According to the present invention, the azomethine compound which is represented by formula M-1 and comprises a pyridine ring bonded to a 1H-pyrazolo[1,5-b][1,2,4]triazole ring through a nitrogen atom can realize a good coupling reaction between the compound of formula II and the compound of formula III and, at the same time, can significantly reduce the production cost of the azomethine compound. The compound of formula I containing a C1-C3 alkoxyphenyl group at the 6-position of the mother nucleus of pyrazolotriazole has high lightfastness and, thus, unlike the azomethine compound with a phenyl group bonded thereto, has no need to introduce various substituents for lightfastness improvement purposes.

The thermal transfer sheet according to the present invention can realize the suppression of catalytic fading to a certain extent and can realize excellent lightfastness of a mixed color, especially black which is a tertiary color, through a combination of the specific yellow dye coloring matter, magenta dye coloring matter, and cyan dye coloring matter.

BEST MODE FOR CARRYING OUT THE INVENTION

Azomethine Compound

The azomethine compound according to the present invention will be described.

The azomethine compound according to the present invention is represented by formula M-I:

[Chemical formula 6]

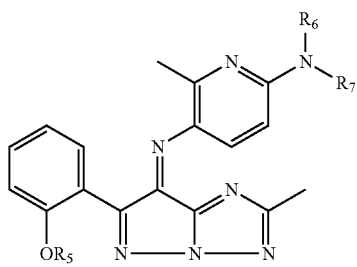

M-I wherein $R_5$ represents a C1-3 (number of carbon atoms) straight chain or branched chain alkyl group; and $R_6$ and $R_7$ each independently represent a C2-4 (number of carbon atoms) alkyl group.

The azomethine compound comprising a 1H-pyrazolo[1,5-b][1,2,4]triazole ring coupler bonded to a pyridyl group through a nitrogen atom, as in the compound of formula M-I, advantageously possesses high lightfastness and can be produced at low cost. The azomethine compound described in Japanese Patent Application Laid-Open No. 239367/1993, in which the unsubstituted pyridyl group is bonded to the coupler, is disadvantageous in that the reaction yield between the coupler and the pyridine ring in the production process of the compound is as low as 1 to 20%. The present inventors have drawn attention to the pyridine ring and have found that the introduction of a methyl group at the o-position of the pyridine ring can significantly improve the degree of conversion of the coupling reaction and can realize a reaction yield of not less than 40%.

According to the present invention, in formula M-I, preferably, $R_6$ and $R_7$ are the same and each represent an alkyl group, more preferably are the same and each represent a propyl group (C3) or a butyl group (C4). The azomethine compound in which both $R_6$ and $R_7$ represent a propyl group or a butyl group is excellent in production cost and lightfastness, as well as in hue sensitivity and dissolvability.

Further, in the present invention, preferably, $R_5$ in formula M-I represents an ethyl group (C2) or a propyl group (C3). When the substituent at the 6-position of the mother nucleus of pyrazolotriazole is an ethoxyphenyl group or a propoxyphenyl group, further improved dissolvability and lightfastness can be realized.

The azomethine compound according to the present invention can be produced according to the following synthesis scheme, that is, by reacting a 1H-pyrazolo[1,5-b][1,2,4]triazole coupler represented by formula (II) with a pyridyldiamino derivative represented by formula (III) using an oxidizing agent in the presence of a base.

[Chemical formula 7]

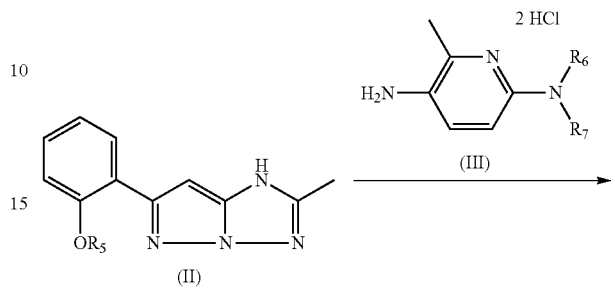

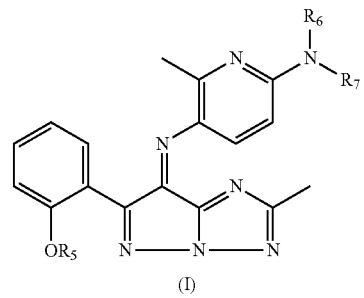

The 1H-pyrazolo[1,5-b][1,2,4]triazole derivative which is a coupler and is represented by formula (II) can be synthesized by a process similar to the process described in Japanese Patent Application Laid-Open No. 239367/1993. For example, the compounds of formulae (II) and (III) can be produced as follows.

At the outset, as shown in the following synthesis scheme, a benzoate compound as a starting compound is reacted with acetonitrile in the presence of potassium t-butoxide to give compound a, and compound a is then reacted with hydrazine to give compound b. Subsequently, compound b is reacted with imidate hydrochloride to give an amidine compound which is then reacted with hydroxylamine to give compound c.

[Chemical formula 8]

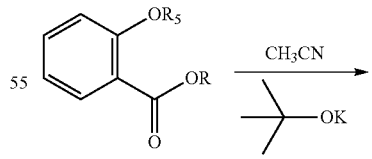

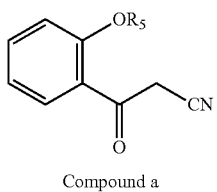

Compound a

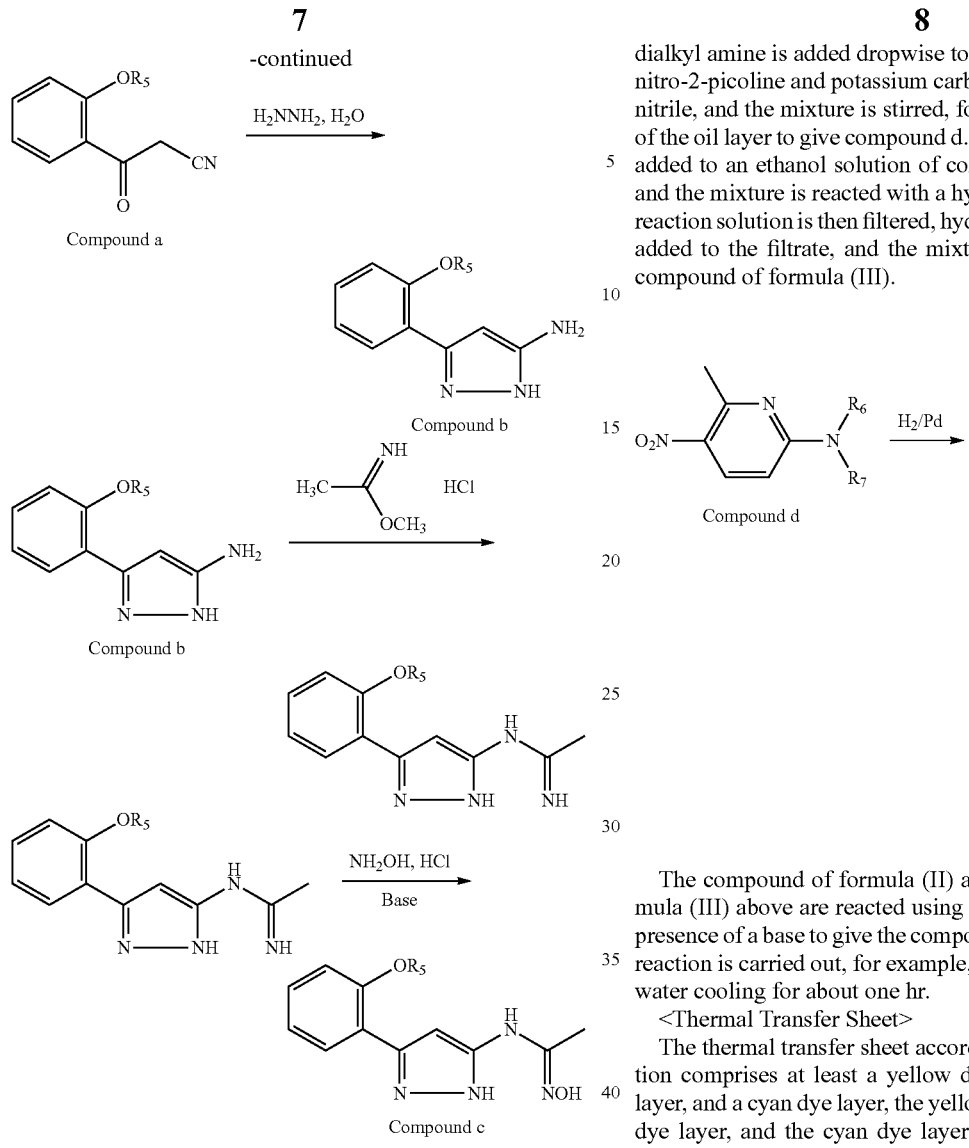

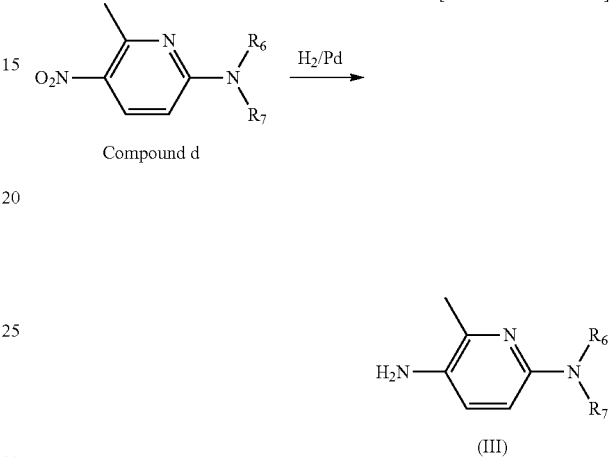

Subsequently, as described below, the compound of formula (II) can be produced by reacting compound c with p-toluenesulfonyl chloride and heating the reaction solution under reflux in the presence of pyridine.

[Chemical formula 9]

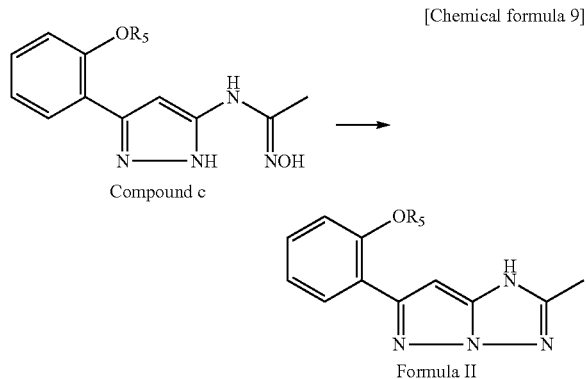

The pyridyldiamine derivative which is the compound of formula (III) can be produced as follows. For example, a dialkyl amine is added dropwise to a solution of 6-chloro-3-nitro-2-picoline and potassium carbonate dissolved in acetonitrile, and the mixture is stirred, followed by the separation of the oil layer to give compound d. Palladium-carbon is then added to an ethanol solution of compound d thus obtained, and the mixture is reacted with a hydrogen gas at 1 atm. The reaction solution is then filtered, hydrochloric acid-dioxane is added to the filtrate, and the mixture is stirred to give the compound of formula (III).

[Chemical formula 10]

The compound of formula (II) and the compound of formula (III) above are reacted using an oxidizing agent in the presence of a base to give the compound of formula M-I. This reaction is carried out, for example, at 40° C. or below under water cooling for about one hr.

<Thermal Transfer Sheet>

The thermal transfer sheet according to the present invention comprises at least a yellow dye layer, a magenta dye layer, and a cyan dye layer, the yellow dye layer, the magenta dye layer, and the cyan dye layer each comprising a base material and a dye layer that contains a dye coloring matter and a binder resin and is provided on the base material, the magenta dye being a dye containing the above azomethine compound. The layers constituting the thermal transfer sheet will be described.

<Base Material>

The base material constituting the thermal transfer sheet according to the present invention functions to support dye layers which will be described later. Conventional materials may be used as the base material. Specifically, any conventional material which has a certain level of heat resistance and strength may be used, and such materials include, for example, resin films such as polyethylene terephthalate films, 1,4-polycyclohexylene dimethylene terephthalate films, polyethylene naphthalate films, polyphenylene sulfide films, polystyrene films, polypropylene films, polysulfone films, aramid films, polycarbonate films, polyvinyl alcohol films, cellulose derivatives such as cellophane and cellulose acetate, polyethylene films, polyvinyl chloride films, nylon films, polyimide films, and ionomer films; papers such as capacitor papers, paraffin papers, and synthetic papers; nonwoven fabrics; and composites composed of paper or nonwoven fabrics and resins.

The thickness of the base material is generally about 0.5 to 50 μm, preferably about 3 to 10 μm.

One surface or both surface of the base material may if necessary be subjected to adhesion treatment. When a dye ink is coated on the base material for dye layer formation purposes, preferably, the base material is subjected to adhesion treatment because the wetting capability, adhesion and the like of coating liquids are likely to be insufficient. Conventional resin surface modification techniques, such as corona discharge treatment, flame treatment, ozone treatment, ultraviolet treatment, radiation treatment, roughening treatment, chemical treatment, plasma treatment, low-temperature plasma treatment, primer treatment, and grafting treatment, as such may be applied to the adhesion treatment. These treatment methods may also be used in a combination of two or more.

The adhesion treatment of the base material may also be carried out by coating an adhesive layer on the base material. The adhesive layer may be formed of the following organic materials or inorganic materials. Examples of organic materials usable herein include polyester resins; polyacrylic ester resins; polyvinyl acetate resins; polyurethane resins; styrene acrylate resins; polyacrylamide resins; polyamide resins; polyether resins; polystyrene resins; polyethylene resins; polypropylene resins; vinyl resins such as polyvinyl chloride resins, polyvinyl alcohol resins, polyvinylpyrrolidone resins, and modification products thereof; and polyvinyl acetal resins such as polyvinyl acetoacetal and polyvinyl butyral. Examples of inorganic materials usable herein include colloidal ultrafine particles of inorganic pigments such as silica (colloidal silica), alumina or alumina hydrate (for example, alumina sol, colloidal alumina, cationic aluminum oxide or its hydrate, or pseudo-boehmite), aluminum silicate, magnesium silicate, magnesium carbonate, magnesium oxide, and titanium oxide.

When the base material is manufactured by stretching a plastic film, the primer treatment may also be carried out, for example, by coating a primer liquid onto an unstretched film and then subjecting the assembly to stretching treatment.

<Dye Layer>

The thermal transfer sheet according to the present invention comprises a base material and at least a yellow dye layer, a magenta dye layer, and a cyan dye layer as dye layers provided on the base material. In the thermal transfer sheet, a conventional black dye layer may be further provided as the dye layer.

The thermal transfer sheet may comprise individual dye layers in a face serial manner provided on a base material. For example, the thermal transfer sheet may comprise a plurality of dye layers such as yellow, magenta, cyan, and black dye layers provided repeatedly in a face serial manner. Alternatively, the thermal transfer sheet may comprise the above plurality of dye layers and additionally a transferable protective layer provided in a face serial manner. A heat-fusion ink layer of black may be additionally provided.

<Yellow Dye Coloring Matter>

The yellow dye layer may comprise a yellow dye coloring matter and a binder resin. Any yellow dye coloring matter may be used without particular limitation, and various heat-fusion yellow dye coloring matters and sublimable yellow dye coloring matters usable in the thermal transfer sheet may be used. In the present invention, among them, yellow dye coloring matters represented by formulae Y-I and/or Y-II are preferred as the yellow dye coloring matter usable in combination with the azomethine-type magenta dye coloring matter.

[Chemical formula 11]

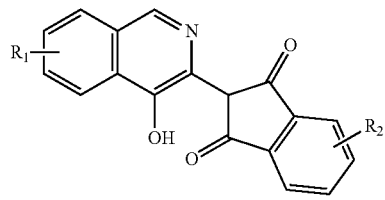

Y-I wherein $R_1$ represents an alkyl group, an aryl group, a hydrogen atom, or a halogen atom; and $R_2$ represents a carbonylamino group or a carbonylalkoxy group.

[Chemical formula 12]

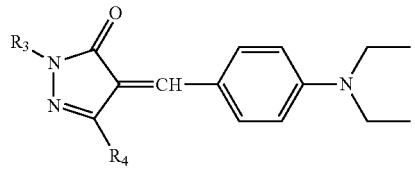

Y-II wherein $R_3$ represents an alkyl group, an aryl group, or a hydrogen atom; and $R_4$ represents an alkyloxy group, an aryloxy group, or an amino group.

In formula Y-I, preferably, $R_1$ represents an alkyl group, more preferably an isopropyl group; and, preferably, $R_2$ represents a carbonyl group, more preferably a carbonylamino group. Yellow dye coloring matters represented by formula Y-I-I are particularly preferred.

[Chemical formula 13]

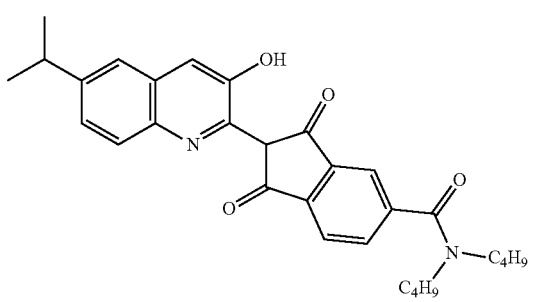

Y-I-I

In formula Y-II, preferably, $R_3$ represents an aryl group, more preferably a phenyl group; and, preferably, $R_4$ represents an alkoxy group. Yellow dye coloring matters represented by formula are particularly preferred.

[Chemical formula 14]

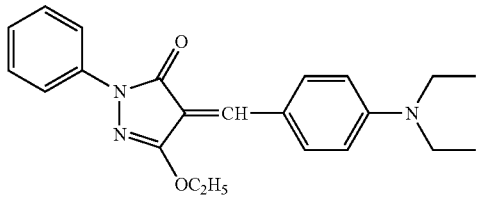

Y-II-I

The yellow dye coloring matter represented by formula Y-II-I may be produced by reacting a pyrazolone derivative with a benzylaldehyde derivative in the presence of a base. Alternatively, the yellow dye coloring matter may be produced by the process described in Japanese Patent No. 1891953.

In the present invention, preferably, the yellow dye coloring matter further comprises dye coloring matters represented by formulae Y-III and/or Y-IV. The combined use of the dye coloring matter represented by formula Y-I-I or Y-II-I and the dye coloring matter represented by formula Y-III and/or formula Y-IV can realize a hue closer to a contemplated yellow hue.

[Chemical formula 15]

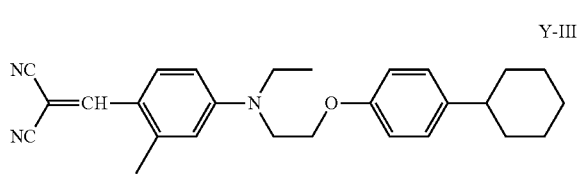

Y-III

[Chemical formula 16]

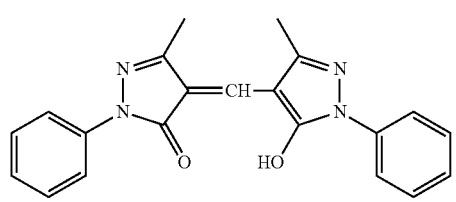

Y-IV

The dye coloring matter represented by formula Y-III is commercially available, and examples of such commercially available products include Disperse Yellow 201 (Macrolex Yellow 6G, manufactured by LANXESS K.K.). Further, the dye coloring matter represented by formula Y-IV is also commercially available, and examples of such commercially available products include Solvent Yellow 93 (for example, Plast Yellow 8000 (tradename), manufactured by Arimoto Chemical Co., Ltd.).

Further, in the present invention, the yellow dye coloring matter may comprise, in addition to yellow dye coloring matters represented by formulae Y-I, Y-II, Y-III, and Y-IV, yellow dye coloring matters represented by formula Y-V which are styryl dyes. This constitution can realize a hue closer to a contemplated yellow hue.

[Chemical formula 17]

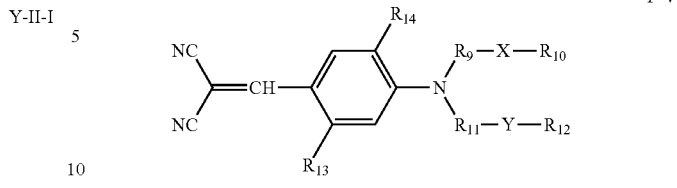

Y-V wherein $R_9$ and $R_{11}$ each independently represent a substituted or unsubstituted alkyl group, a substituted or unsubstituted cycloalkyl group, a substituted or unsubstituted aryl alkyl group, a substituted or unsubstituted heterocyclic aryl group, or Rt that represents an alkyl group interrupted by at least one of —O—, —O.CO—, —CO.O—, —SO$_2$—, —OSO$_2$—, —NH—, and —.CO.O—;

X and Y each independently represent a substituted or unsubstituted cycloalkyl group, a substituted or unsubstituted aryl group, a substituted or unsubstituted heterocyclic group, a hydrogen atom, a hydroxyl group, a cyano group, a nitro group, or Rt that is as defined above;

$R_{10}$ and $R_{12}$, when X and Y do not represent a hydrogen atom, a hydroxyl group, a cyano group, or a nitro group, each independently represent a hydrogen atom, a hydroxyl group, a cyano group, a nitro group, a substituted or unsubstituted alkyl group, a substituted or unsubstituted cycloalkyl group, a substituted or unsubstituted aryl group, a substituted or unsubstituted heterocyclic group, or Rt that is as defined above;

$R_{13}$ represents a substituted or unsubstituted alkyl group, a hydroxyl group, —NHCOR$_9$, —OR$_9$, —COR$_9$, —NHSO$_2$R$_9$, or —CO.OR$_9$ wherein R$_9$ is as defined above; and $R_{14}$ represents an alkoxy group that may form a ring together with $R_9$, $R_{10}$, $R_{11}$, or $R_{12}$ or —NHCORt wherein Rt is as defined above.

The compounds represented by formula Y-V may be produced by the process described by Japanese Patent Applications No. 238170/1993.

Among the styryl dyes represented by formula Y-V, coloring matter compounds represented by formulae Y-V-I and Y-V-II are more preferred.

[Chemical formula 18]

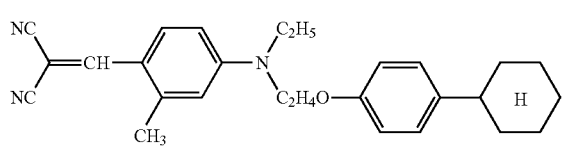

Y-V-I

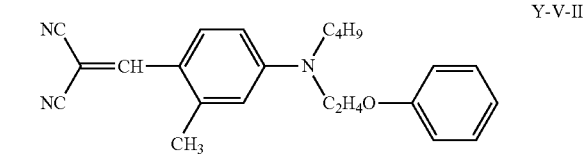

Y-V-II

Further, in the present invention, in addition to the above yellow dye coloring matters, the pyradone azo dye represented by formula Y-VI may be used in combination with the yellow dye coloring matters represented by formulae Y-I and/or Y-II. The combined use of these dyes can realize a hue closer to a contemplated yellow hue. The pyradone azo dye represented by formula Y-VI may be produced by the process described in Japanese Patent Application Laid-Open No. 11450/1996.

[Chemical formula 19]

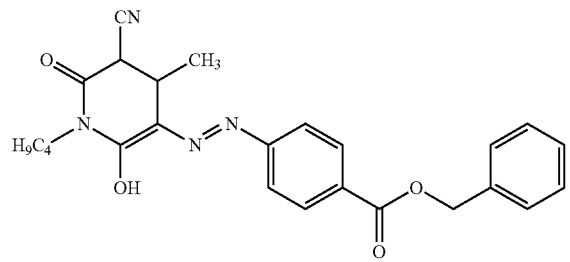

Y-VI

In the present invention, the above yellow dye coloring matters may be used in combination with other dye coloring matters. Examples of such other dye coloring matters include conventional yellow dye coloring matters, for example, diarylmethane coloring matters; triarylmethane coloring matters; thiazole coloring matters; merocyanine coloring matters; methine coloring matters such as pyrazolone methine; indoaniline coloring matters; azomethine coloring matters typified by acetophenoneazomethine, pyrazoloazomethine, imidazoleazomethine, imidazoazomethine, and pyridoneazomethine coloring matters; xanthene coloring matters; oxazine coloring matters; cyanostyrene coloring matters typified by dicyanostyrene and tricyanostyrene coloring matters; thiazine coloring matters; azine coloring matters; acridine coloring matters; benzeneazo coloring matters; azo coloring matters other than those general formula I such as pyridoneazo, thiopheneazo, isothiazoleazo, pyrroleazo, pyrrazoleazo, imidazoleazo, thiadiazoleazo, triazoleazo, and disazo coloring matters; spiropyran coloring matters; indolinospiropyran coloring matters; fluoran coloring matters; rhodaminelactam coloring matters; naphthoquinone coloring matters; anthraquinone coloring matters; and quinophthalone coloring matters.

<Magenta Dye Coloring Matter>

In the thermal transfer sheet according to the present invention, the magenta dye layer comprises the magenta dye coloring matter represented by formula M-I and a binder resin.

In the present invention, the magenta dye coloring matter may comprise, in addition to the coloring matter represented by formula M-I, dye coloring matters represented by formula M-II. The combined use of these two types of magenta dye coloring matters can realize a hue closer to a contemplated hue and, at the same time, can realized further improved lightfastenss.

[Chemical formula 20]

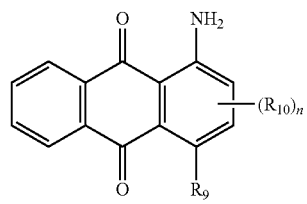

M-II

In the formula, $R_9$ represents a substituted or unsubstituted alkoxycarbonyl group, a substituted or unsubstituted amino group, a hydroxy group, a substituted or unsubstituted alkoxy group, a substituted or unsubstituted aryloxy group, a substituted or unsubstituted alkyl group, a substituted or unsubstituted cycloalkyl group, a heterocyclic group, or a halogen atom; $R_{10}$ represents an amino group or a hydroxyl group; and n is an integer of 2 or less, provided that, when a plurality of $R_{10}$s are present, $R_{10}$s may be the same or different.

In the present invention, preferably, $R_9$ represents a hydroxyl group or an amino group; and, preferably, $R_{10}$ represents a phenoxy group; and n is 1 or 2. Dye coloring matters represented by formulae M-II-I and/or M-II-II are particularly preferred as the dye coloring matter of formula M-II.

[Chemical formula 21]

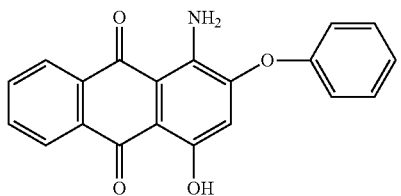

M-II-I

[Chemical formula 22]

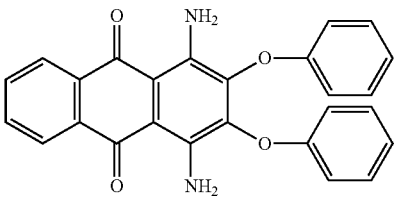

M-II-II

An anthraquinone dye such as Disperse Red 60 may be mentioned as the magenta dye coloring matter represented by formula M-II-I, and an anthraquinone dye such as Disperse Violet 26 may be mentioned as the magenta dye coloring matter represented by formula M-II-II.

Further, in the present invention, in addition to the coloring matter compounds represented by formula M-II, imidazoleazo dye coloring matters and azomethine dye coloring matters represented by formula M-III may be mentioned as the magenta dye coloring matter usable in combination with the coloring matter represented by formula M-I. The combined use of these dyes can realize a hue closer to a contemplated hue and, at the same time, can further improve the lightfastness.

[Chemical formula 23]

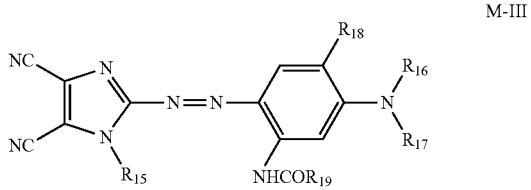

M-III wherein, $R_{15}$, $R_{18}$, and $R_{17}$ each independently represent a hydrogen atom, a substituted or unsubstituted alkyl group, a cycloalkyl group, an allyl group, or a substituted or unsubstituted phenyl group; $R_{18}$ represents a hydrogen atom, an alkyl group, an alkoxy group, or a halogen atom; and $R_{19}$ represents a hydrogen atom, an alkyl group, a trifluoromethyl group, an alkoxy group, or a substituted or unsubstituted vinyl group. The coloring matter compounds represented by formula M-III may be produced by the process described in Japanese Patent Application Laid-Open No. 241784/1990.

Further, in the present invention, among the coloring matter compounds of formula M-III usable in combination with the dye coloring matters of formula M-I, imidazoleazo-type dye coloring matters represented by formula M-III-I are more preferred. The imidazoleazo-type dye coloring matters represented by formula M-III-I may be produced by the process described in Japanese Patent Application Laid-Open No. 241784/1990 (dye of No. 25 in Table 2 in the working example).

[Chemical formula 24]

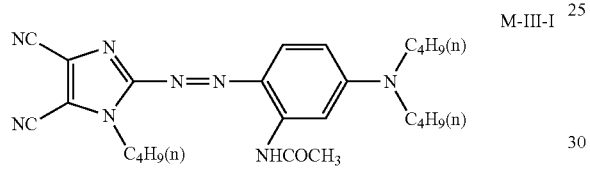

M-III-I

Coloring matter compounds represented by formula M-IV are suitable as the azomethine-type dye coloring matters usable in combination with the dye coloring matters represented by formula M-I. The coloring matter compounds represented by formula M-IV may be produced by the process described in Japanese Patent No. 3013137.

[Chemical formula 25]

M-IV

<Cyan Dye Layer>

The cyan dye layer comprises a cyan dye coloring matter and a binder resin. The cyan dye coloring matter usable herein is not particularly limited, and various heat-fusion cyan dye coloring matters and sublimable cyan dye coloring matters usable in the thermal transfer sheet are usable. In the present invention, among them, cyan dye coloring matters represented by formula C-I are preferred as the cyan dye coloring matter usable in combination with the yellow dye coloring matter and the magenta dye coloring matter.

[Chemical formula 26]

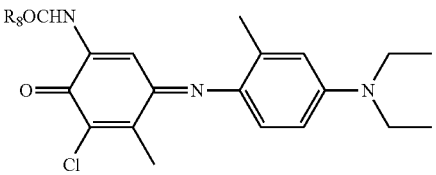

C-I

In the formula, preferably; $R_8$ represents an alkyl or aryl group, more preferably a methyl or phenyl group. Cyan dye coloring matters represented by formula C-I-I or C-I-II are particularly preferred.

[Chemical formula 27]

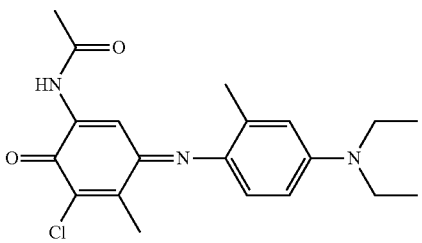

C-I-I

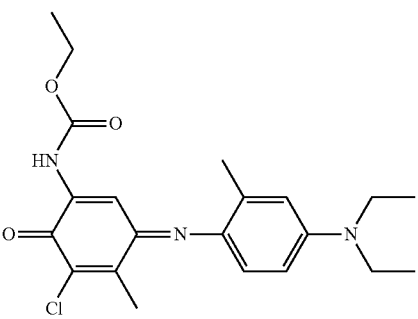

C-I-II

The cyan dye coloring matter represented by formula C-I may be produced in the same manner as in the production of the indoaniline compound described in Japanese Patent No. 2572025. The cyan dye coloring matter represented by formula C-I-I or C-I-II may be produced in the same manner as in the production of the indoaniline compound described in Japanese Patent No. 5045436.

In addition to the above cyan dye coloring matter, other cyan dye coloring matters may also be added as the cyan dye coloring matter. The other cyan dye coloring matter is not particularly limited as long as the cyan dye coloring matter is a dye that is usable in the conventional thermal transfer sheet and is thermally transferable by sublimation. The other cyan dye coloring matter may be properly selected by taking into consideration, for example, hue, sensitivity in printing, light-fastness, storage stability, and solubility in the binder.

In the present invention, the cyan dye coloring matter may comprise, in addition to the cyan coloring matter of formula C-1 or C-I-I, dye coloring matters represented by formulae C-II and/or C-III:

[Chemical formula 28]

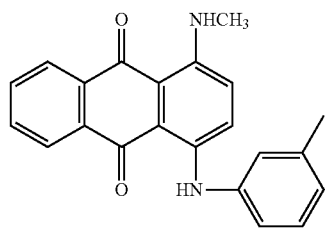

C-II

[Chemical formula 29]

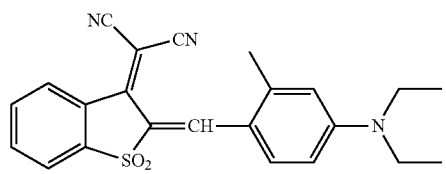

C-III

Cyan dye coloring matters represented by formula C-II are commercially available, and examples thereof include Solvent Blue 63. Examples of cyan dye coloring matters represented by formula C-III include Disperse Blue 354 (Foron Brilliant Blue S-R, manufactured by Clariant (Japan) K.K.).

In addition to the above cyan dye coloring matter, other cyan dye coloring matters may also be added as the cyan dye coloring matter. The other cyan dye coloring matter is not particularly limited as long as the cyan dye coloring matter is a dye that is usable in the conventional thermal transfer sheet and is thermally transferable by sublimation. The other cyan dye coloring matter may be properly selected by taking into consideration, for example, hue, sensitivity in printing, lightfastness, storage stability, and solubility in the binder.

Preferably, the content of each dye is such that satisfactory density can be obtained as images (reflection density of yellow, magenta, and cyan=1.8 or more as measured in terms of ISO status A density), although the preferred content varies depending upon a combination of the dye with the base material and the primer. The content ranges will be described later.

Each of the dye layers comprises the specific dye and, further, a binder resin. The binder resin is not particularly limited, and conventional binder resins are usable. Examples of such binder resins include, for example, cellulosic resins such as methylcellulose, ethylcellulose, hydroxymethylcellulose, hydroxyethylcellulose, hydroxypropylcellulose, cellulose acetate, and cellulose butyrate; vinyl resins such as polyvinyl alcohol, polyvinyl acetate, polyvinyl butyral, polyvinyl acetal, polyvinylpyrrolidone, and polyacrylamide; polyester resins; and phenoxy resins.

Releasable graft copolymers may be also mentioned as the binder resin. The releasable graft copolymers may also be mixed as a release agent into the dye layer. The releasable graft copolymers are such that at least one releasable segment selected from a polysiloxane segment, a carbon fluoride segment, a hydrocarbon fluoride segment, and a long-chain alkyl segment has been graft polymerized to the main chain of the polymer constituting the binder resin. Among them, a graft copolymer produced by grafting a polysiloxane segment onto the main chain of a polyvinyl acetal is preferred.

If necessary, additives such as release agents, inorganic fine particles, and organic fine particles may also be used in each of the dye layers. Release agents include the above-described releasable graft copolymers, silicone oils, and phosphoric esters. Examples of such inorganic fine particles include carbon black, aluminum, and molybdenum disulfide. Examples of such organic fine particles include polyethylene wax.

Each of the dye layers is formed using a dye ink containing a specific dye, a binder resin, optionally additives, and a solvent. Any conventional solvent known as the material for dye inks may be used as the solvent without particular limitation. Examples of such solvents include acetone, methanol, water, methyl ethyl ketone, toluene, ethanol, isopropyl alcohol, cyclohexanone, dimethylformamide (DMF), ethyl acetate, and mixed solvents thereof. Among them, a mixed solvent composed of methyl ethyl ketone and toluene is preferred.

In the dye ink containing the yellow dye coloring matter, the content of the yellow dye coloring material is preferably 50 to 300 parts by mass, more preferably 85 to 250 parts by mass, based on 100 parts by mass of the binder resin. Further, in the yellow dye ink, the content of the yellow dye coloring matter is preferably 0.5 to 15% by mass. Further, in the yellow dye ink, preferably, the total content of the dye such as the yellow dye coloring matter and the binder resin, that is, the solid content, is 2 to 30% by mass, more preferably 5 to 15% by mass. When the yellow dye ink contains two or more dye coloring matters, both the content of the yellow dye and the solid content represent the total content for the dye coloring matters.

In the dye ink containing the magenta dye coloring matter, the content of the magenta dye coloring matter is preferably 50 to 300 parts by mass, more preferably 85 to 250 parts by mass, based on 100 parts by mass of the binder resin. When the magenta dye coloring matter contains two or more dye coloring matters, both the content of the magenta dye coloring matter and the solid content represent the total content for the dye coloring matters.

In the dye ink containing the cyan dye coloring matter, the content of the cyan dye coloring matter is preferably 50 to 300 parts by mass, more preferably 85 to 250 parts by mass, based on 100 parts by mass of the binder resin. In the cyan dye ink, the total content of the cyan dye coloring matter and the binder resin, that is, the solid content, is preferably approximately 2 to 30% by mass, more preferably 5 to 15% by mass. When the cyan dye coloring matter contains two or more dye coloring matters, both the content of the cyan dye coloring matter and the solid content represent the total content for the dye coloring matters.

Each of the dye inks may be prepared by conventional production methods, for example, using paint shakers, propeller-type stirrers, dissolvers, homomixers, ball mills, bead mills, sand mills, two-roll mills, three-roll mills, ultrasonic dispersing machines, kneaders, line mixers, or twin screw extruders.

Each of the dye layers may be formed by coating the dye ink onto the base material by a conventional method such as wire bar coating, gravure printing, or reverse roll coating using a gravure plate.

Gravure coating is preferred as the coating method. Any drying conditions may be adopted for drying of the coating without particular limitation. Preferably, however, the coating is dried at a temperature of 60 to 120° C. for approximately one sec to 5 min. When drying of the dye inks is unsatisfactory, smudge or the transfer of the dye ink onto the backside of the sheet in winding and the retransfer of the transferred dye ink, in rewinding, onto a dye layer having a different hue, that is, kickback, sometimes occurs.

Preferably, each of the dye inks is coated at a coverage of approximately 0.2 to 3.0 g/m$^2$, more preferably approximately 0.4 to 1.0 g/m$^2$, on a dry basis.

<Other Layers>

In the thermal transfer sheet according to the present invention, a heat-resistant slip layer may be provided on the base material on its surface remote from the surface on which each of the dye layers is formed. The heat-resistant slip layer is provided to prevent the occurrence of problems derived from heat of a thermal head in the thermal transfer, for example, sticking or cockling during printing.

The heat-resistant slip layer is composed mainly of a heat-resistant resin. The heat-resistant resin is not particularly limited, and examples thereof include, for example, polyvinyl butyral resins, polyvinyl acetoacetal resins, polyester resins, vinyl chloride-vinyl acetate copolymer resins, polyether resins, polybutadiene resins, styrene-butadiene copolymer resins, acrylic polyols, polyurethane acrylates, polyester acrylates, polyether acrylates, epoxy acrylates, prepolymers of urethane or epoxy, nitrocellulose resins, cellulose nitrate resins, cellulose acetate propionate resins, cellulose acetate butyrate resins, cellulose acetate-hydrodiene phthalate resins, cellulose acetate resins, aromatic polyamide resins, polyimide resins, polyamide-imide resins, polycarbonate resins, and chlorinated polyolefin resins.

The heat-resistant slip layer may comprise the heat-resistant resin and additionally additives such as slipperiness-imparting agents, crosslinking agents, release agents, organic powders and inorganic powders mixed into the heat-resistant resin.

The heat-resistant slip layer may be generally formed by adding the heat-resistant resin and optionally the above-described slipperiness-imparting agents and additives into the solvent, dissolving or dispersing the ingredients in the solvent to prepare a coating liquid for the heat-resistant slip layer, then coating the coating liquid for the heat-resistant slip layer onto the base material, and drying the coating.

The solvent in the coating liquid for the heat-resistant slip layer may be the same as the solvent used in the dye inks.

The coating liquid for the heat-resistant slip layer may be coated, for example, by wire bar coating, gravure printing, screen printing, or reverse roll coating using a gravure plate. Among these coating methods, gravure coating is preferred.

Preferably, the coating liquid for the heat-resistant slip layer is coated at a coverage of 0.1 to 3 g/m$^2$, more preferably not more than 1.5 g/m$^2$, on a dry basis.

As long as the thermal transfer sheet according to the present invention comprises the dye layers provided on the base material, for example, an undercoating layer may be provided between the base material and the dye layer. The undercoating layer is not particularly limited, and, in the provision of the undercoating layer, a composition that can improve the adhesion between the base material and the dye layer is properly selected.

In the thermal transfer sheet according to the present invention, in order that a protective layer which can protect an image surface after image formation can be transferred, a transferable protective layer may be further provided in a face serial relationship with the dye layers. The construction and the formation of the transferable protective layer are not particularly limited and may be selected by a conventional technique depending upon properties of the base material sheet, dye layers and the like used. When the base material film is not releasable, preferably, a peel layer is provided between the base material film and the transferable protective layer to improve the transferability of the transferable protective layer.

In the thermal transfer sheet according to the present invention, predetermined sites of the base material on its surface remote from the dye layers can be heated and pressed by a thermal head or the like to transfer the dyes, in the layers, in the sites corresponding to the printing areas onto a transfer object and thus to performing printing.

For example, thermal transfer image receiving sheets may be used as the transfer object. The thermal transfer image receiving sheet is not particularly limited as long as the recording surface is receptive to dyes. For example, a sheet comprising a base material of paper, a metal, glass, a synthetic resin or the like and a dye-receptive layer provided on at least one surface of the base material may be mentioned as the transfer object. In particular, when the thermal transfer sheet according to the present invention is applied to a thermal transfer image receiving sheet prepared using an aqueous coating liquid for dye-receptive layer formation, the lightfastness can be further improved. The printer used in the thermal transfer is not particularly limited, and any conventional thermal printer may be used.

EXAMPLES

The present invention is further illustrated by the following Examples that are not intended as a limitation of the invention.

<Preparation of Yellow Inks>

Individual ingredients were mixed with stirring according to formulations specified in Table 1 below to prepare yellow inks YE1 to YE3. In the table, the numeral values are in parts by weight.

TABLE 1

|  |  | YE1 | YE2 | YE3 |
|---|---|---|---|---|
| Yellow dye | Formula Y-I-I | — | 5.0 | 4.0 |
|  | Formula Y-II-I | 2.5 | — | — |
|  | Macrolex Yellow 6G (Formula Y-III) | — | 3.0 | — |
|  | Plast Yellow 93 (Formula Y-IV) | 2.5 | — | — |
|  | Formula Y-VI | — | — | 3.0 |
| Binder | Polyvinyl acetal resin*1 | 70.0 | 70.0 | 70.0 |
| Solvent | Toluene | 12.5 | 11.0 | 11.5 |
|  | Methyl ethyl ketone | 12.5 | 11.0 | 11.5 |

*1 S-lec KS-5, 5% varnish, manufactured by Sekisui Chemical Co., Ltd.

In Table 1, yellow dyes represented by formulae Y-I-I and were produced according to the process described in Japanese Patent No. 5045436 and had the following chemical structural formulae.

[Chemical formula 30]

Y-I-I
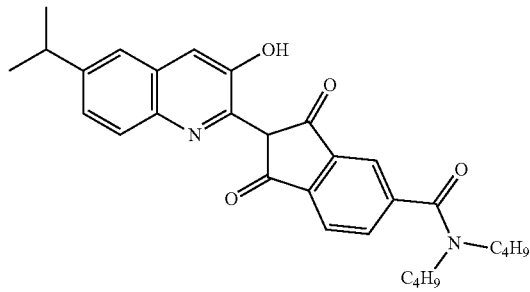

Y-II-I
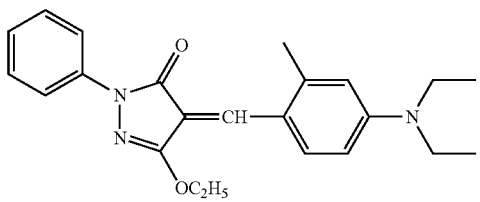

<Preparation of Magenta Inks>

In the same manner as described above, individual ingredients were mixed with stirring according to formulations specified in Tables 2 and 3 below to prepare magenta inks MG1 to MG26. In the table, the numeral values are in parts by weight.

TABLE 2

|  |  | MG1 | MG2 | MG3 | MG4 | MG5 | MG6 | MG7 |
|---|---|---|---|---|---|---|---|---|
| Magenta dye | M-I-I | 2.60 | — | — | — | — | — | — |
|  | M-I-II | — | 2.60 | — | — | — | — | — |
|  | M-I-III | — | — | 2.60 | — | — | — | — |
|  | M-I-IV | — | — | — | 2.60 | — | — | — |
|  | M-I-V | — | — | — | — | 2.60 | — | — |
|  | M-I-VI | — | — | — | — | — | 2.60 | — |
|  | M-I-VII | — | — | — | — | — | — | 2.60 |
|  | M-I-VIII | — | — | — | — | — | — | — |
|  | M-II-I | 2.30 | 2.30 | 2.30 | 2.30 | 2.30 | 2.30 | 2.30 |
|  | M-II-II | 3.40 | 3.40 | 3.40 | 3.40 | 3.40 | 3.40 | 3.40 |
|  | M-III-I | — | — | — | — | — | — | — |
|  | Comparative dye 1 | — | — | — | — | — | — | — |
|  | Comparative dye 2 | — | — | — | — | — | — | — |
| Binder | Polyvinyl acetal resin *1 | 70.0 | 70.0 | 70.0 | 70.0 | 70.0 | 70.0 | 70.0 |
| Solvent | Toluene | 10.85 | 10.85 | 10.85 | 10.85 | 10.85 | 10.85 | 10.85 |
|  | Methyl ethyl ketone | 10.85 | 10.85 | 10.85 | 10.85 | 10.85 | 10.85 | 10.85 |
|  |  | MG8 | MG9 | MG10 | MG11 | MG12 | MG13 | MG14 |
| Magenta dye | M-I-I | — | 1.30 | — | — | — | — | — |
|  | M-I-II | — | — | 1.30 | — | — | — | — |
|  | M-I-III | — | — | — | — | — | — | — |
|  | M-I-IV | — | — | — | — | — | — | — |
|  | M-I-V | — | — | — | — | — | — | — |
|  | M-I-VI | — | — | — | — | — | 2.60 | — |
|  | M-I-VII | — | — | — | — | — | — | 2.60 |
|  | M-I-VIII | 2.60 | — | — | — | — | — | — |
|  | M-II-I | 2.30 | 2.30 | 2.30 | 2.30 | 2.30 | — | — |
|  | M-II-II | 3.40 | 3.40 | 3.40 | 3.40 | 3.40 | — | — |
|  | M-III-I | — | 1.30 | — | — | — | — | — |
|  | Comparative dye 1 | — | — | — | 2.60 | — | — | — |
|  | Comparative dye 2 | — | — | — | — | 2.60 | — | — |
| Binder | Polyvinyl acetal resin *1 | 70.0 | 70.0 | 70.0 | 70.0 | 70.0 | 70.0 | 70.0 |
| Solvent | Toluene | 10.85 | 10.85 | 10.85 | 10.85 | 10.85 | 13.70 | 13.70 |
|  | Methyl ethyl ketone | 10.85 | 10.85 | 10.85 | 10.85 | 10.85 | 13.70 | 13.70 |

*1: S-lec KS-5, 5% varnish, manufactured by Sekisui Chemical Co., Ltd.

TABLE 3

| | | MG15 | MG16 | MG17 | MG18 | MG19 | MG20 | MG21 | MG22 | MG23 | MG24 | MG25 | MG26 |
|---|---|---|---|---|---|---|---|---|---|---|---|---|---|
| Magenta dye | M-I-I | 2.17 | — | — | — | — | — | — | — | 1.08 | — | — | — |
| | M-I-II | — | 2.17 | — | — | — | — | — | — | — | 1.08 | — | — |
| | M-I-III | — | — | 2.17 | — | — | — | — | — | — | — | — | — |
| | M-I-IV | — | — | — | 2.17 | — | — | — | — | — | — | — | — |
| | M-I-V | — | — | — | — | 2.17 | — | — | — | — | — | — | — |
| | M-I-VI | — | — | — | — | — | 2.17 | — | — | — | — | — | — |
| | M-I-VII | — | — | — | — | — | — | 2.17 | — | — | — | — | — |
| | M-I-VIII | — | — | — | — | — | — | — | 2.17 | — | — | — | — |
| | M-II-I | 1.92 | 1.92 | 1.92 | 1.92 | 1.92 | 1.92 | 1.92 | 1.92 | 1.92 | 1.92 | 1.92 | 1.92 |
| | M-II-II | 2.84 | 2.84 | 2.84 | 2.84 | 2.84 | 2.84 | 2.84 | 2.84 | 2.84 | 2.84 | 2.84 | 2.84 |
| | M-III-I | — | — | — | — | — | — | — | — | 1.08 | — | — | — |
| | Comparative dye 1 | — | — | — | — | — | — | — | — | — | 1.08 | 2.17 | — |
| | Comparative dye 2 | — | — | — | — | — | — | — | — | — | — | 2.17 | — |
| Binder | Polyvinyl acetal resin *[1] | 70.0 | 70.0 | 70.0 | 70.0 | 70.0 | 70.0 | 70.0 | 70.0 | 70.0 | 70.0 | 70.0 | 70.0 |
| Solvent | Toluene | 10.04 | 10.04 | 10.04 | 10.04 | 10.04 | 10.04 | 10.04 | 10.04 | 10.04 | 10.04 | 10.04 | 10.04 |
| | Methyl ethyl ketone | 10.04 | 10.04 | 10.04 | 10.04 | 10.04 | 10.04 | 10.04 | 10.04 | 10.04 | 10.04 | 10.04 | 10.04 |

*[1]: S-lec KS-5, 5% varnish, manufactured by Sekisui Chemical Co., Ltd.

Magenta dyes in Tables 2 and 3 had the following chemical structure formulae.

[Chemical formula 31]

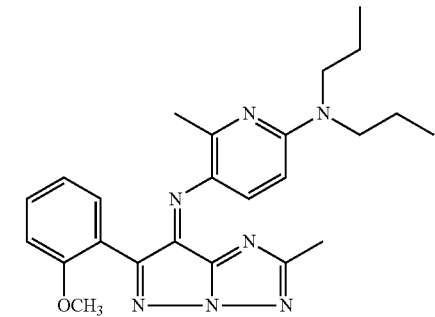

M-I-I

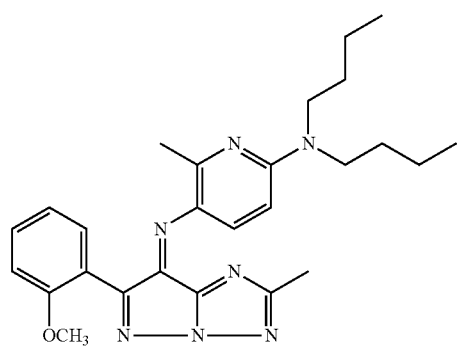

M-I-II

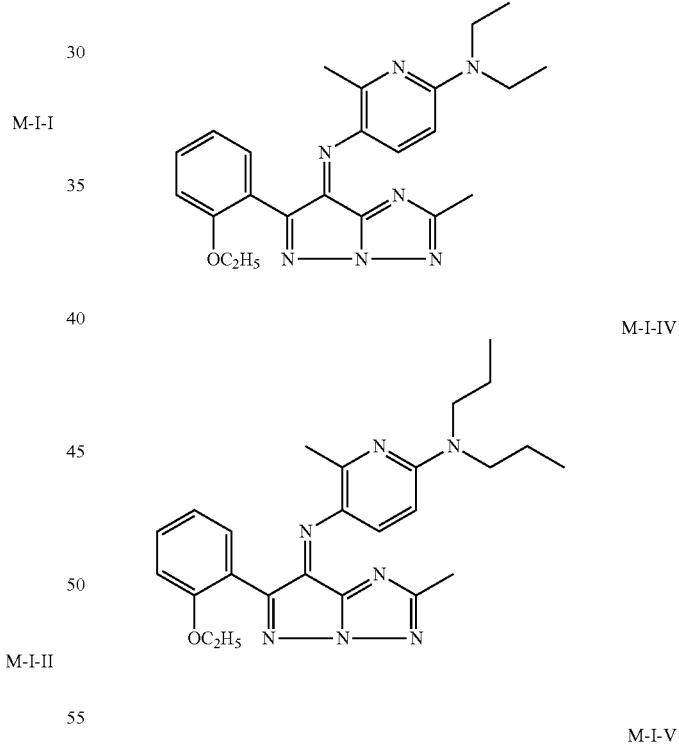

M-I-III

M-I-IV

M-I-V

M-I-VI

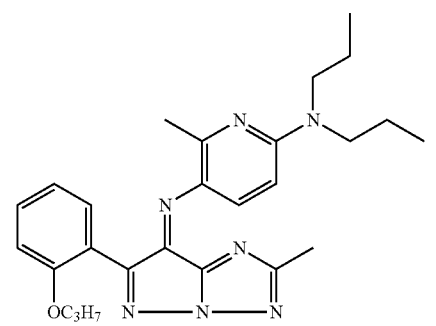

M-I-VII

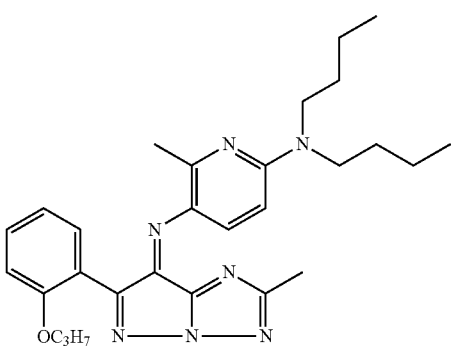

M-I-VIII

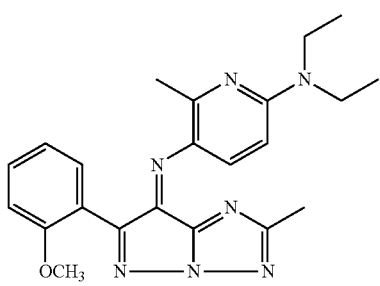

The compound represented by formula M-I-IV was produced as follows.

Ethyl 2-ethoxybenzoate (100 g, 0.52 mol), 500 ml of toluene, and 21.1 g (0.52 mol) of acetonitrile were charged into a 1000-ml four-neck flask, and the mixture was stirred in an ice bath. Thereafter, 57.7 g (0.52 mol) of potassium t-butoxide was introduced over a period of about 10 min. The reaction solution was in a white slurry state. The reaction system was then returned to room temperature before stirring for one hr. Water (100 ml) was added dropwise to the reaction system in the water bath over a period of 3 min. As a result, the reaction solution was separated into two layers. The aqueous layer was recovered, the oil layer was washed twice with 50 ml of water, and the washed water was also recovered as the aqueous layer.

The aqueous layer thus obtained was neutralized to approximately pH 1 by the addition of 50 ml (0.55 mol) of 11.1 M concentrated hydrochloric acid in a water bath, resulting in the precipitation of crystals. The crystals were collected by filtration and were dried at 60° C. overnight to give 57.2 g (0.32 mol) of contemplated compound A1. The yield was 59%, and the purity was 94% in terms of simple area ratio determined by HPLC. The synthesis scheme is as follows.

[Chemical formula 32]

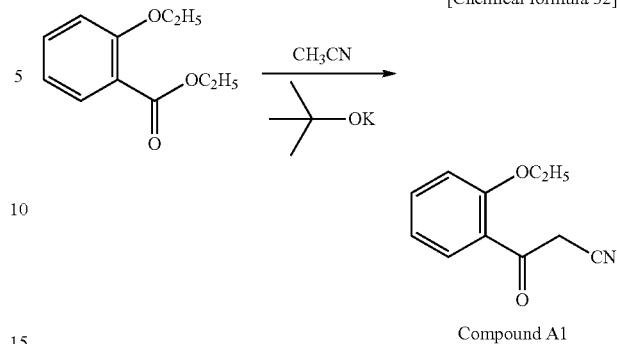

Compound A1 (89.0 g, 0.47 mol) and 90 ml of methanol were introduced into a 500-ml four-neck flask, and the mixture was stirred. The reaction solution was in a brown slurry form. Hydrazine monohydrate (23.5 g, 0.47 mol) was then added dropwise to the reaction solution in a water bath over a period of about 3 min. The mixture was then heated under reflux for 2.5 hr. The reaction solution was concentrated at about 50° C. by a rotary evaporator to give an oil. The oil was dissolved in 400 ml of ethyl acetate, followed by separation with 100 ml of a saturated aqueous sodium bicarbonate solution. The oil layer was then dried over 100 ml of saturated brine and was concentrated at 40° C. by a rotary evaporator to give 90 g of contemplated compound A2. The yield was 94%, and the purity was 93% in terms of simple area ratio determined by HPLC. The synthesis scheme is as follows.

[Chemical formula 33]

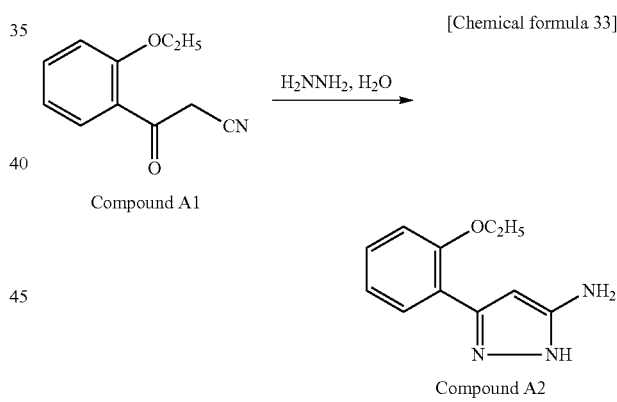

Subsequently, 94 g (0.46 mol) of compound A2 and 500 ml of methanol were introduced into 5000-ml four-neck flask. Thereafter, 50.39 g (0.46 mol) of imidate hydrochloride (compound A3) obtained from acetonitrile and methanol was added thereto in a water bath, and a reaction was allowed to proceed at room temperature for one hr to give compound A4. A separately prepared solution which was composed of 34.5 g (0.46 mol) of hydroxylamine hydrochloride, 44.4 g (0.23 mol) of 28% sodium methylate-methanol solution, and 350 ml of methanol and was filtered was added dropwise to the reaction system containing compound A4 over a period of about 5 min in a water bath. The reaction system was then heated (65° C.) with stirring under reflux for 5 hr. The reaction solution as such was cooled to room temperature and was continuously stirred overnight (12.5 hr). Thereafter, 2.4 L of water was added to the reaction solution. As a result, solid was precipitated from the reaction solution, resulting in the formation of slurry. The slurry was filtered, and the resultant crystals were suspended in 40 ml of methanol with heating under reflux for one hr. Thereafter, the suspension was allowed to stand for cooling while continuing stirring. When the suspension was cooled to room temperature, the suspension was stirred while cooling in an ice bath. The suspension was then filtered to give 24.3 g of contemplated compound A5. The yield was 20%, and the purity was 96% in terms of simple area ratio determined by HPLC. The synthesis scheme is as follows.

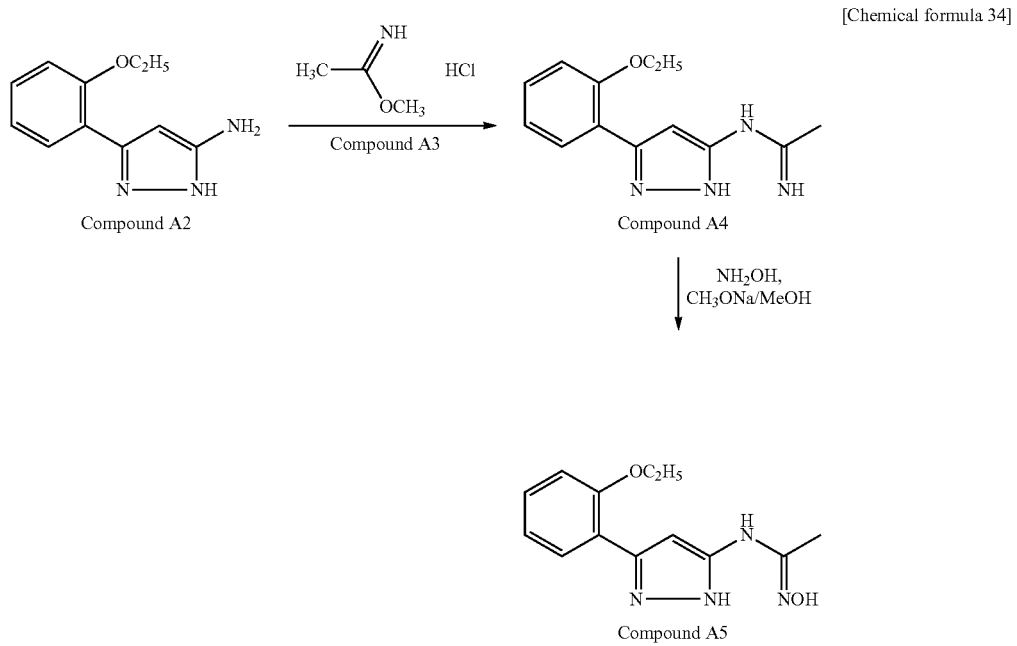

Subsequently, 9.8 g (38 mmol) of compound A5, 10 ml of acetonitrile, and 10 ml of dimethylacetamide were charged into 500-ml four-neck flask, and the mixture was stirred. The reaction solution was in a brown slurry state. Thereafter, 7.2 g (38 mmol) of p-toluenesulfonyl chloride was introduced over a period of about 10 min in a water bath. Pyridine (3.0 g, 38 mmol) was then added dropwise to the reaction solution over a period of 3 min in a water bath. Here again, the reaction solution was in a brown slurry state. The reaction solution was stirred at room temperature for 30 min, and the disappearance of compound A5 was confirmed by TLC (chloroform/methanol 6/1). Thereafter, 70 ml of methanol was added to the reaction system, and 3.0 g (38 mmol) of pyridine was added dropwise thereto over a period of 3 min. The reaction solution was then heated (temperature 65° C.) with stirring under reflux for 2.5 hr. The disappearance of compound A6 was confirmed by TLC. Thereafter, 300 ml of ethyl acetate was added to the reaction solution, and the mixture was washed thrice with 300 ml of water. The oil layer was recovered and was concentrated at about 50° C. by a rotary evaporator to give an oil. The oil was suspended in 10 ml of methanol with heating (65° C.) under reflux for 20 min. The suspension was cooled, and the reaction system was then filtered. The resultant crystals were washed with methanol cooled to 0° C. to give 3.76 g of contemplated compound A7. The yield was 41%, and the purity was 91% in terms of simple area ratio determined by HPLC. The synthesis scheme is as follows.

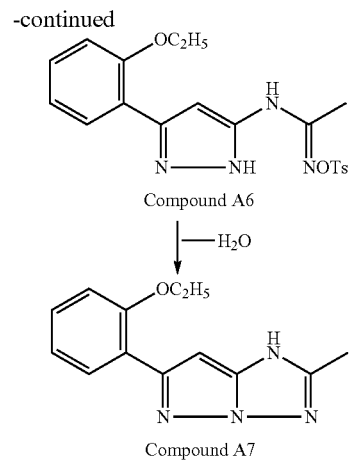

6-Chloro-3-nitro-2-picoline (10 g, 58 mmol), 100 ml of acetonitrile, and 5.1 g (30 mmol) of potassium carbonate were introduced into a 500-ml four-neck flask, and the mixture was stirred under water cooling. Thereafter, 5.9 g (0.58 mmol) of di-n-propylamine was added dropwise to the reaction system, and the mixture was then stirred with heating (temperature 65° C.) under reflux for 8 hr. The disappearance of 6-chloro-3-nitro-2-picoline was confirmed by HPLC. Thereafter, the reaction solution was filtered, and the filtrate thus obtained was separated with 100 ml of water. The oil layer was recovered and concentrated at about 50° C. by a rotary evaporator to give 12.1 g of an oil. The oil was analyzed by ESIMS and consequently was found to be contemplated compound A8. The yield was 88%, and the purity was 96% in terms of simple area ratio determined by HPLC. The synthesis scheme is as follows.

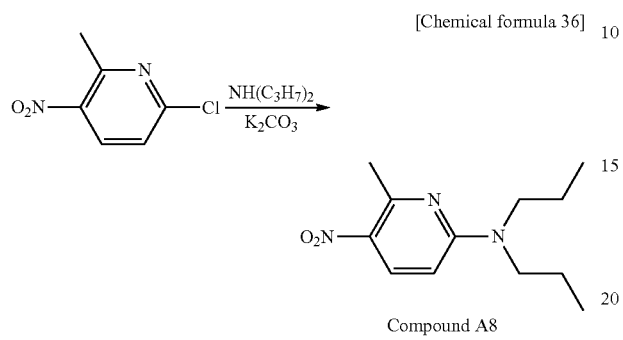

Compound A8

Next, 10 g (47 mmol) of compound A8, 100 ml of ethanol, and 3.0 g (5 wt %) of palladium-carbon were introduced into a 500-ml four-neck flask, and the mixture was reacted with a hydrogen gas (one atm). The reaction solution as such was stirred at room temperature for 3 hr, and the disappearance of compound A8 was confirmed by TLC (chloroform/methanol 6/1). The reaction solution was filtered, and 100 ml of 4 N hydrochloric acid-dioxane was added to the filtrate. The mixture was stirred at room temperature for 20 min. As a result, solid was precipitated from the reaction solution, resulting in the formation of slurry. The slurry as such was stirred in an ice bath for one hr and was filtered to give 9.32 g of contemplated compound A9. The yield was 96%. The synthesis scheme is as follows.

Methanol (20 ml) was added to 1.8 g (7.4 mmol) of compound A7 thus obtained, and 2.07 g of sodium hydroxide, and 4.15 g (14.8 mmol) of compound A9 were added thereto. Thereafter, an aqueous solution prepared by dissolving 4.40 g (18.5 mmol) of sodium persulfate in 9 ml of water was added dropwise to the reaction solution. The reaction solution was stirred for one hr and was filtered. The solid thus obtained was suspended in hot water at 40° C. for one hr. The suspension was filtered, and the resultant solid was dissolved in toluene and was purified by chromatography on silica gel to give 2.12 g of contemplated compound A. The yield was 64%. The compound thus obtained was identified by $^1$H HNR. The results of the analysis were as follows.

$^1$H NMR, δ (ppm) (multiplicity, integral value) (CDCl$_3$)
9.23 (d, 1H), 7.58 (dd, 1H), 7.43 (m, 1H), 7.02 (m, 2H), 6.62 (d, 1H), 4.07 (q, 4H), 3.55 (q, 4H), 2.58 (s, 3H), 2.42 (s, 3H), 1.69 (m, 4H), 1.28 (t, 3H), 0.95 (t, 3H)

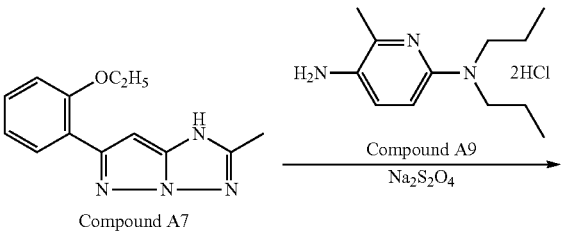

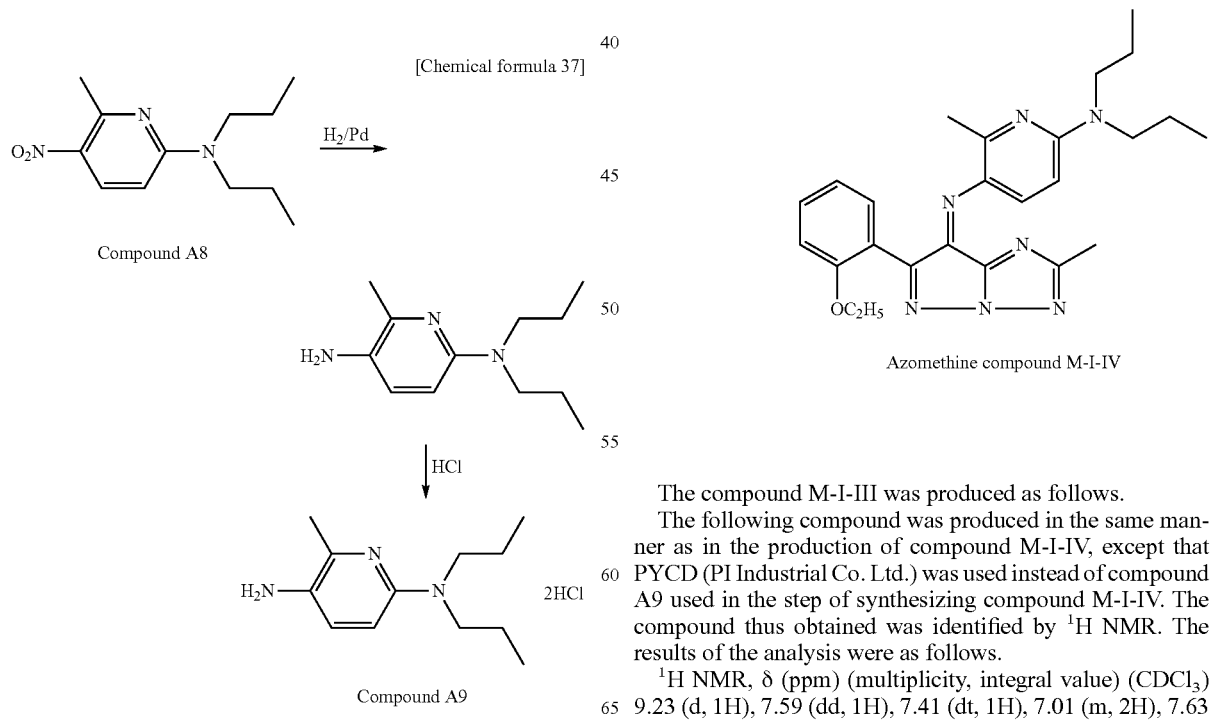

The compound M-I-III was produced as follows.

The following compound was produced in the same manner as in the production of compound M-I-IV, except that PYCD (PI Industrial Co. Ltd.) was used instead of compound A9 used in the step of synthesizing compound M-I-IV. The compound thus obtained was identified by $^1$H NMR. The results of the analysis were as follows.

$^1$H NMR, δ (ppm) (multiplicity, integral value) (CDCl$_3$)
9.23 (d, 1H), 7.59 (dd, 1H), 7.41 (dt, 1H), 7.01 (m, 2H), 7.63 (d, 1H), 4.05 (q, 2H), 3.64 (q, 4H), 2.56 (s, 1H), 2.41 (s, 1H), 1.24 (m, 9H)

[Chemical formula 39]

Azomethine compound M-I-III

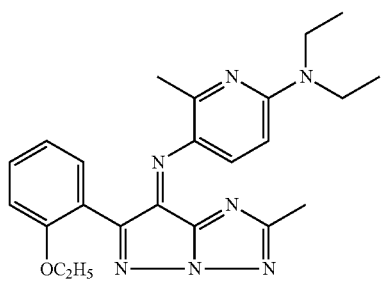

The compound M-I-VI was produced as follows.

The following compound M-I-VI was produced in the same manner as in the production of compound M-I-III, except that compound C7 was used instead of compound A7 used in the synthesis of compound M-I-III. The compound thus obtained was identified by $^1$H NMR. The results of the analysis were as follows.

$^1$H NMR, δ (ppm) (multiplicity, integral value) (CDCl$_3$) 9.25 (d, 1H), 7.59 (ss, 1H), 7.43 (dt, 1H), 7.03 (m, 2H), 6.64 (d, 1H), 4.96 (t, 2H), 3.56 (q, 4H), 2.60 (s, 3H), 2.43 (s, 3H), 1.69 (m, 6H), 0.97 (t, 3H), 0.89 (t, 3H)

[Chemical formula 40]

Azomethine compound M-I-IV

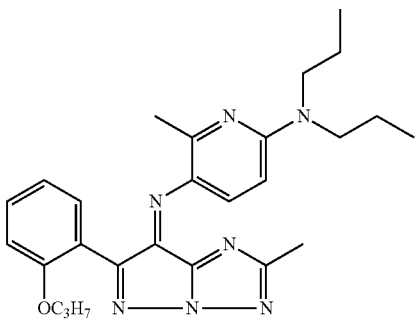

Compound C7 used above was synthesized as follows. At the outset, 100 g (0.52 mol) of methyl 2-n-propoxybenzoate, 300 ml of toluene, and 21.1 g (0.52 mol) of acetonitrile were introduced into a 1000-ml four-neck flask, and the mixture was stirred in an ice bath. Thereafter, 57.8 g (0.52 mol) of potassium t-butoxide was added thereto over a period of about 10 min. The reaction solution was in a white slurry state. The reaction system was then returned to room temperature before stirring for one hr. The completion of the reaction was confirmed by HPLC. Water (100 ml) was added dropwise to the reaction system in the water bath over a period of 3 min. As a result, the reaction solution was separated into two layers. The aqueous layer was recovered, the oil layer was washed with 100 ml of water, and the washed water was also recovered as the aqueous layer. The aqueous layer thus obtained was neutralized to approximately pH 2 by the addition of concentrated hydrochloric acid in a water bath, resulting in the precipitation of crystals from the aqueous layer. The crystals were dissolved in 300 ml of ethyl acetate, again followed by separation. The aqueous layer was extracted twice with 200 ml of ethyl acetate. The oil layer was concentrated at about 50° C. by a rotary evaporator to give an oil. The oil was solid at room temperature. Thus, 73.9 g of compound C1 was obtained as the oil. The yield was 71%, and the purity was 90% in terms of simple area ratio determined by HPLC. The synthesis scheme is as follows.

[Chemical formula 41]

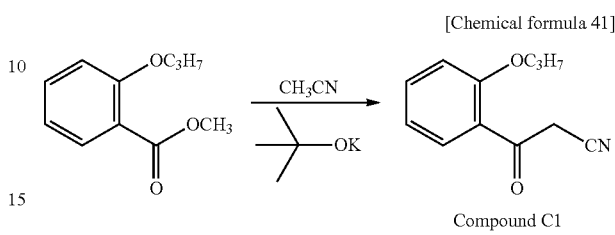

Compound C1

Subsequently, 70 ml of methanol was added to 72 g (0.35 mol) of compound C1 contained in a 500-ml four-neck flask in an ice bath. Thereafter, 17.7 g (0.35 mol) of hydrazine monohydrate was added dropwise to the reaction solution over a period of 5 min in a water bath. The mixture was then heated under reflux for 2.5 hr. The reaction solution was concentrated at 50° C. by a rotary evaporator to give an oil. The oil was dissolved in 300 ml of ethyl acetate, and 100 ml of a saturated aqueous sodium bicarbonate solution was added to the solution, followed by separation. The oil layer thus obtained was dried over saturated brine and was concentrated at 50° C. by a rotary evaporator. The oil was dissolved in 300 ml of toluene, and 2000 ml of hexane was added dropwise to give 51.2 g of contemplated compound C2. The yield was 67%.

[Chemical formul 42]

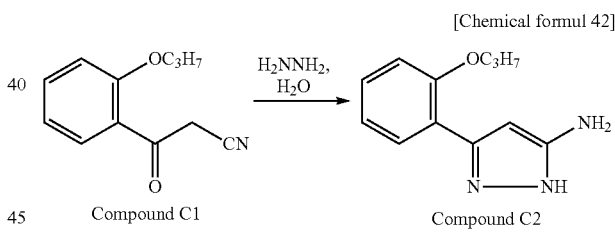

Compound C1                Compound C2

Compound C2 (50 g, 0.23 mol) and 250 ml of methanol were introduced into a 1000-ml four-neck flask. Thereafter, 25.2 g (0.23 mol) of compound A3 was added to the reaction system in a water bath, and a reaction was allowed to proceed at room temperature for one hr to give compound C4. A separately prepared solution which was composed of 16.0 g (0.23 mol) of hydroxylamine hydrochloride, 36.8 g (0.23 mol) of 28% sodium methylate, and 150 ml of methanol and was filtered was added dropwise to the reaction system containing compound A4 over a period of about 5 min in a water bath. The reaction system was then heated (65° C.) with stirring under reflux for 3 hr, and the reaction system was filtered. The filtrate was concentrated at about 50° C. by a rotary evaporator to give an oil. MeOH (32 ml) was added to the oil for recrystallization to give 16.8 g of contemplated compound C5. The yield was 27%, and the purity was 94% in terms of simple area ratio determined by HPLC. The synthesis scheme is as follows.

[Compound formula 43]

Compound C2 + Compound A3 →

Compound C5

↓

Compound C4

↓ NH₂OH, CH₃ONa/MeOH

Compound C5

Compound C5 (16.0 g, 58 mmol), 16 ml of acetonitrile, and 16 ml of dimethylacetamide were introduced into a 500-ml four-neck flask, and the mixture was stirred. The reaction solution was in a brown slurry state. Thereafter, 11.0 g (58 mmol) of p-toluenesulfonyl chloride was introduced to the reaction system in a water bath over a period of about 10 min. Subsequently, 4.6 g (58 mmol) of pyridine was added dropwise to the reaction system in a water bath over a period of 3 min. Here again, the reaction solution was in a brown slurry state. The slurry was stirred at room temperature for 30 min. Thereafter, the disappearance of compound C5 was confirmed by TLC (chloroform/methanol 6/1). Thereafter, 128 ml of methanol was added to the reaction system, and 4.6 g (58 mmol) of pyridine was added dropwise to the reaction system over a period of 3 min. Thereafter, the mixture was heated (temperature 65° C.) with stirring under reflux for 2.5 hr. The disappearance of compound C5 was confirmed by TLC. Ethyl acetate (300 ml) was then added to the reaction system, and the reaction solution was washed thrice with 300 ml of water. The oil layer was concentrated at about 50° C. by a rotary evaporator to give an oil. Methanol (10 ml) was added to the oil, and the mixture was suspended with heating (65° C.) under reflux for 20 min. After cooling, the resultant crystals were collected by filtration and were washed with methanol cooled to 0° C. to give 6.8 g of contemplated compound C7. The yield was 41%, and the purity was 98% in terms of simple area ratio determined by HPLC. The synthesis scheme is as follows.

[Chemical formula 44]

Compound C5 → (TsCl, pyridine) → Compound C6 → (pyridine) → Compound C7

The compound M-I-V was produced as follows.
The following compound M-I-V was produced in the same manner as in the production of compound M-I-VI, except that PYCD (PI Industrial Co. Ltd.) used in the synthesis of compound M-I-III was used instead of compound A9 used in the synthesis of compound M-I-VI. The compound thus obtained was identified by ¹H NMR. The results of the analysis were as follows.

¹H NMR, δ (ppm) (multiplicity, integral value) (CDCl₃) 9.26 (d, 1H), 7.60 (d, 1H), 7.45 (t, 1H), 7.04 (m, 2H), 6.66 (d, 1H), 3.96 (t, 2H), 3.67 (q, 4H), 2.59 (s, 3H), 2.44 (s, 3H), 1.69 (q, 2H), 1.26 (t, 6H), 0.89 (t, 3H)

[Chemical formula 45]

Azomethine compound M-I-V

The compound M-I-VII was produced as follows.
The following compound M-I-VII was produced in the same manner as in the synthesis of compound M-I-VI, except that compound A10 was used instead of compound A9 used in the synthesis of compound M-I-VI. Compound A10 was produced by allowing dibutylamine to act instead of dipropylamine in the synthesis of compound A8 in compound M-I-IV and performing the same reaction as in the synthesis of compound A9.

The compound M-I-VII thus obtained was identified by $^1$H NMR. The results of the analysis were as follows.

$^1$H NMR, δ (ppm) (multiplicity, integral value) (CDCl$_3$) 9.23 (d, 1H), 7.58 (d, 1H), 7.43 (t, 1H), 7.02 (m, 2H), 6.62 (d, 2H), 3.95 (t, 2H), 3.58 (q, 4H), 2.59 (s, 3H), 2.41 (s, 3H), 1.65 (m, 6H), 1.37 (m, 4H), 0.97 (t, 6H), 0.88 (t, 3H)

[Chemical formula 46]

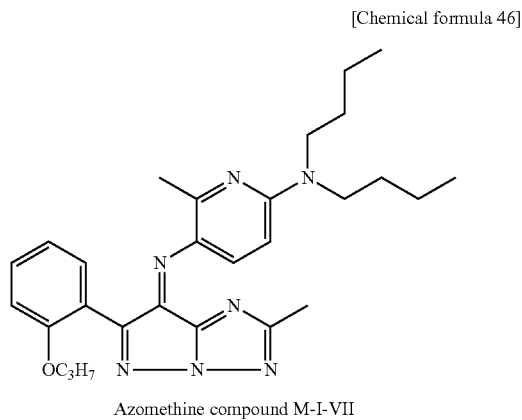

Azomethine compound M-I-VII

The compound M-I-I was produced as follows.

The following compound M-I-I was produced in the same manner as in the production of compound M-I-IV, except that compound E7 was used instead of compound A7 used in the step of synthesizing compound M-I-IV. The compound thus obtained was identified by $^1$H NMR. The results of the analysis were as follows.

$^1$H NMR, δ (ppm) (multiplicity, integral value) (CDCl$_3$) 9.24 (d, 1H), 7.60 (t, 1H), 7.47 (m, 1H), 7.05 (m, 2H), 6.63 (d, 1H), 3.83 (s, 3H), 3.56 (m, 4H), 2.58 (s, 3H), 2.43 (s, 3H), 1.70 (m, 4H), 0.96 (t, 6H)

[Chemical formula 47]

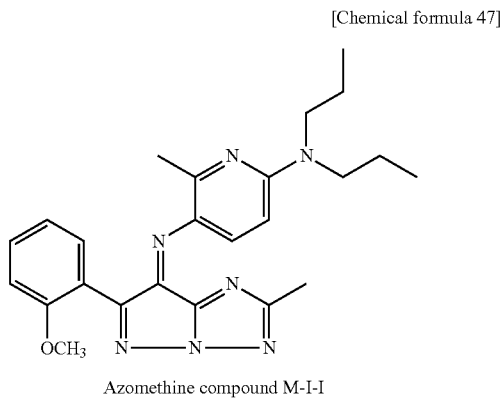 [SMILES: CCCN(CCC)c1ccc(/N=C2/C(c3ccccc3OC)=Nn3nc(C)nc32)c(C)n1]

Azomethine compound M-I-I

Compound E7 used above was synthesized as follows. At the outset, 86.4 g (0.52 mol) of 2-methyl anisate, 300 ml of toluene, and 21.1 g (0.52 mol) of acetonitrile were introduced into a 1000-ml four-neck flask, and the mixture was stirred in an ice bath. Thereafter, 57.8 g (0.52 mol) of potassium t-butoxide was added to the reaction system over a period of about 10 min. The reaction solution was in a white slurry state. The reaction system was then returned to room temperature before stirring for one hr. The completion of the reaction was confirmed by HPLC. Water (100 ml) was added dropwise to the reaction system in the water bath over a period of 3 min. In this state, stirring was continued. As a result, the crystals in the reaction system were dissolved, and the reaction solution was separated into two layers. The reaction solution was separated, and the aqueous layer was recovered. The oil layer was washed with 100 ml of water, and the washed water was also recovered as the aqueous layer. The aqueous layer thus obtained was neutralized to approximately pH 2 by the addition of concentrated hydrochloric acid in a water bath, resulting in the precipitation of crystals. The crystals were dissolved in 300 ml of ethyl acetate, again followed by separation. The aqueous layer was extracted twice with 200 ml of ethyl acetate. The oil layer was concentrated at about 50° C. by a rotary evaporator to give 56.5 g of compound E1. The yield was 62%, and the purity was 93% in terms of simple area ratio determined by HPLC. The synthesis scheme is as follows.

[Chemical formula 48]

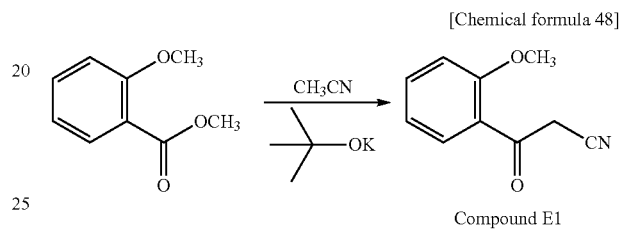

Compound E1

Subsequently, 55 ml of methanol was added to 55 g (0.31 mol) of compound E1 contained in a 500-ml four-neck flask in a water bath. Thereafter, 15.5 g (0.31 mol) of hydrazine monohydrate was added dropwise to the reaction system over a period of 5 min in a water bath. The mixture was then heated under reflux for 2.5 hr. The reaction solution was concentrated at 50° C. by a rotary evaporator to give an oil. The oil was dissolved in 300 ml of ethyl acetate, and 100 ml of a saturated aqueous sodium bicarbonate solution was added to the solution, followed by separation. The oil layer thus obtained was dried over saturated brine and was concentrated at 50° C. by a rotary evaporator to give 58.0 g of contemplated compound E2. The yield was 99%.

[Chemical formula 49]

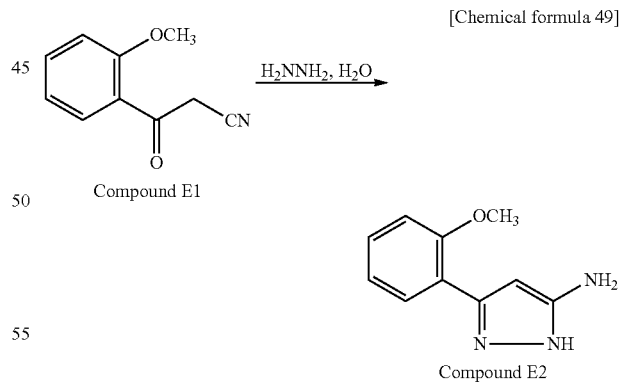

Subsequently, 43.5 g (0.23 mol) of compound E2 and 200 ml of methanol were introduced into a 1000-ml four-neck flask. Thereafter, 25.2 g (0.23 mol) of compound A3 was added to the reaction system in a water bath, and a reaction was allowed to proceed at room temperature for one hr to give compound E4. A separately prepared solution which was composed of 16.0 g (0.23 mol) of hydroxylamine hydrochloride, 36.8 g (0.23 mol) of 28% sodium methylate, and 150 ml of methanol and was filtered was added dropwise to the reaction system containing compound E4 over a period of about 5 min in a water bath. The reaction system was then heated (65° C.) with stirring under reflux for 3 hr, and the reaction solution was concentrated at about 50° C. by a rotary evaporator to give an oil. MeOH (22 ml) was added to the oil for recrystallization to give 16.4 g of contemplated compound E5. The yield was 29%, and the purity was 94% in terms of simple area ratio determined by HPLC. The synthesis scheme is as follows.

[Chemical formula 50]

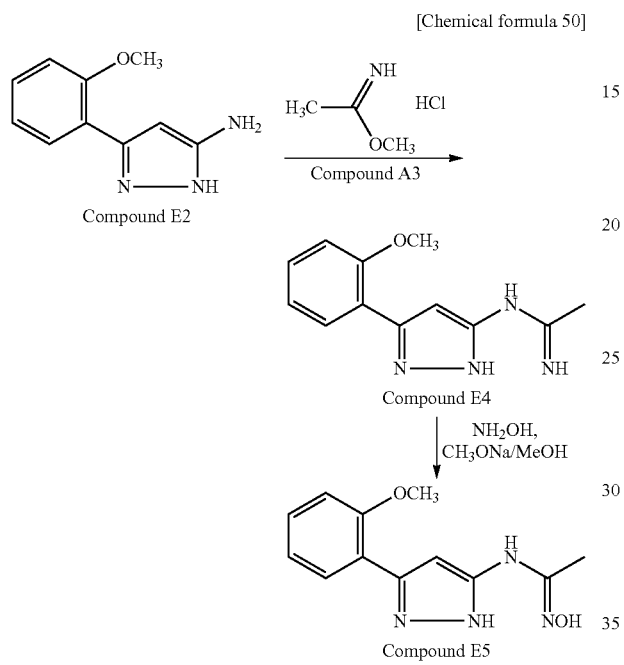

Compound E5 (15.0 g, 61 mmol), 15 ml of acetonitrile, and 15 ml of dimethylacetamide were introduced into a 500-ml four-neck flask, and the mixture was stirred. The reaction solution was in a brown slurry state. Thereafter, 11.0 g (58 mmol) of p-toluenesulfonyl chloride was added to the reaction system in a water bath over a period of about 10 min. Subsequently, 4.6 g (58 mmol) of pyridine was added dropwise to the reaction system in a water bath over a period of 3 min. Here again, the reaction solution was in a brown slurry state. The slurry was stirred at room temperature for 30 min. Thereafter, the disappearance of compound E5 was confirmed by TLC (chloroform/methanol 6/1). Thereafter, 128 ml of methanol was added to the reaction system, and 4.6 g (58 mmol) of pyridine was added dropwise to the reaction system over a period of 3 min. Thereafter, the mixture was heated (temperature 65° C.) with stirring under reflux for 2.5 hr. The disappearance of compound E6 was confirmed by TLC. Ethyl acetate (300 ml) was then added to the reaction system, and the reaction system was washed thrice with 300 ml of water. The oil layer was concentrated at about 50° C. by a rotary evaporator to give an oil. Methanol (10 ml) was added to the oil, and the mixture was suspended with heating (65° C.) under reflux for 20 min. After cooling, the resultant crystals were collected by filtration and were washed with methanol cooled to 0° C. to give 10.4 g of contemplated compound E7. The yield was 75%, and the purity was 96% in terms of simple area ratio determined by HPLC. The synthesis scheme is as follows.

[Chemical formula 51]

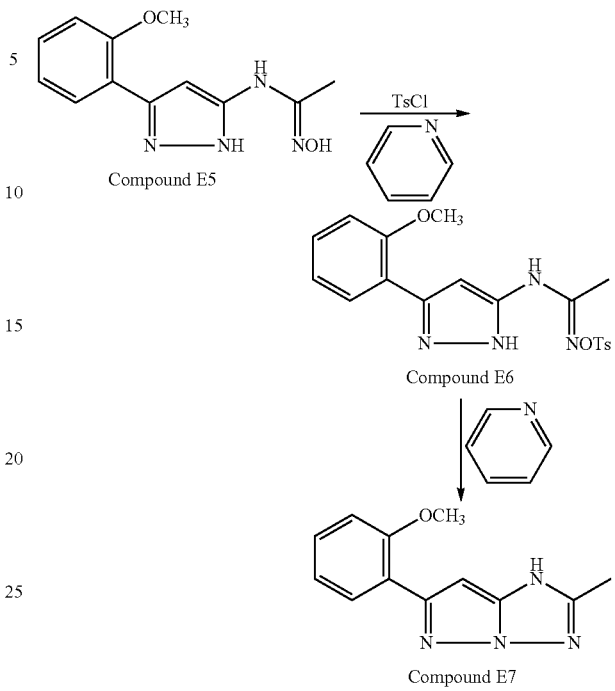

The compound M-I-II was produced as follows.
The following compound M-I-II was produced in the same manner as in the production of compound M-I-I, except that compound A10 used in the step of synthesizing compound M-I-VII was used instead of compound A9 used in the step of synthesizing compound M-I-I. The compound thus obtained was identified by $^1$H NMR. The results of the analysis were as follows.

$^1$H NMR, δ (ppm) (multiplicity, integral value) (CDCl$_3$) 9.39 (d, 1H), 7.60 (m, 1H), 7.46 (t, 1H), 7.06 (m, 2H), 6.63 (d, 1H), 3.83 (s, 1H), 3.58 (m, 4H), 2.58 (s, 3H), 1.63 (m, 4H), 1.37 (m, 4H), 0.97 (t, 6H)

[Chemical formula 52]

Azomethine compound M-I-II

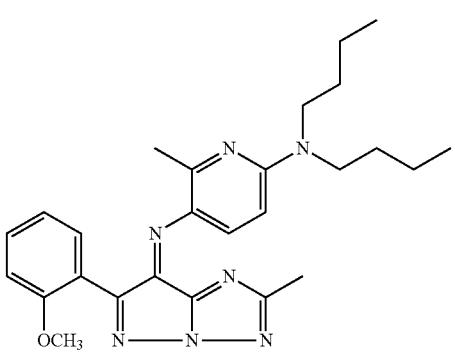

The compound M-I-VIII was produced as follows.
The following compound M-I-VIII was produced in the same manner as in the production of compound M-I-I, except that PYCD (PI Industrial Co. Ltd.) used in the step of synthesizing compound M-I-III was used instead of compound A9 used in the step of synthesizing compound M-I-I. The compound thus obtained was identified by $^1$H NMR. The results of the analysis were as follows.

$^1$H NMR, δ (ppm) (multiplicity, integral value) (CDCl$_3$) 9.26 (d, 1H), 7.60 (m, 1H), 7.47 (t, 1H), 7.05 (m, 2H), 6.65 (d, 1H), 3.83 (s, 1H), 3.69 (m, 4H), 2.57 (s, 3H), 2.44 (s, 3H), 1.25 (t, 6H)

[Chemical formula 53]

Azomethine compound M-I-VIII

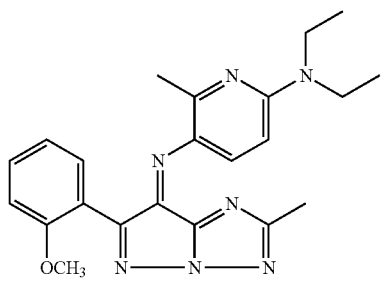

In Tables 2 and 3, the dye represented by formula M-III was produced according to the process described in Japanese Patent Application Laid-Open No. 241784/1990 (Dye of No. 25 in Table 2 in the working example).

[Chemical formula 54]

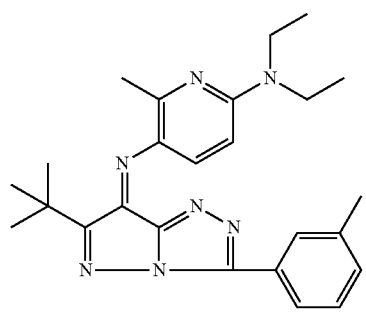

M-III-I

Comparative dye 1 in Tables 2 and 3 was a magenta coloring matter (dye of D-9 described in the working example of Japanese Patent No. 3013137) represented by the following formula.

[Chemical formula 55]

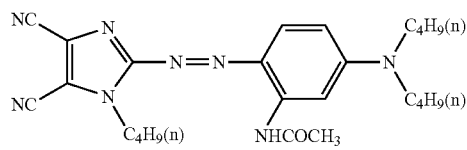

Comparative dye 2 in Tables 2 and 3 was a magenta coloring matter (comparative coloring matter A described in Japanese Patent No. 3013137) represented by the following formula.

[Chemical formula 56]

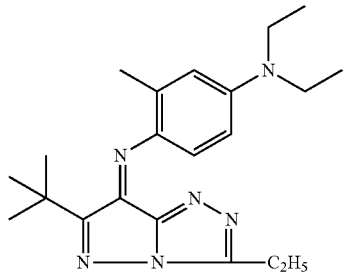

<Preparation of Cyan Inks>

In the same manner as described above, individual ingredients were mixed with stirring according to formulations specified in Table 4 below to prepare cyan inks CY1 to CY3. In the table, the numeral values are in parts by weight.

TABLE 4

|  |  | CY1 | CY2 | CY3 |
|---|---|---|---|---|
| Cyan dye | Formula C-I-I | 3.0 | 3.0 | — |
|  | Formula C-I-II | — | — | 3.0 |
|  | Solvent Blue 63 (Formula C-II) | 4.0 | 3.0 | 4.0 |
|  | Disperse Blue 354 (Formula C-III) | — | 1.5 | — |
| Binder | Polyvinyl acetal resin*1 | 70.0 | 70.0 | 70.0 |
| Solvent | Toluene | 11.5 | 11.25 | 11.5 |
|  | Methyl ethyl ketone | 11.5 | 11.25 | 11.5 |

*1 S-lec KS-5, 5% varnish, manufactured by Sekisui Chemical Co., Ltd.

In Table 4, cyan dyes represented by formulae C-I-I and C-I-II had the following chemical structural formulae and were produced according to the process described in Japanese Patent No. 5045436.

[Chemical formula 57]

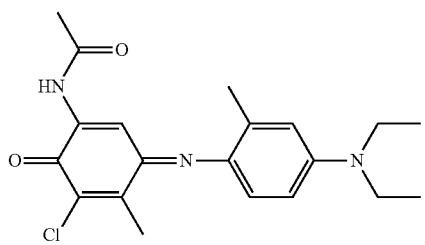
C-I-I

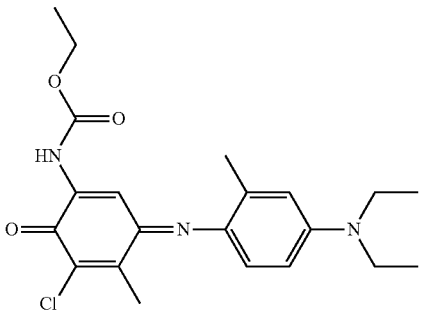
C-I-II

<Preparation of Thermal Transfer Sheet>

A coating liquid, for heat-resistant slip layer formation, having the following composition was coated on one surface of a 4.5 μm-thick polyethylene terephthalate (PET) film at a coverage of 1.0 g/m² on a dry basis, and the coated film was then dried to form a heat-resistant slip layer. The mixing amounts described below are by mass. Subsequently, each of the inks prepared above was gravure coated on the PET film on its surface remote from the heat-resistant slip layer at a coverage of 0.8 g/m² on a dry basis, followed by drying at 80° C. for 2 min to form a dye layer.

<Coating Liquid for Heat-Resistant Slip Layer>
Polyvinyl butyral resin 13.6 parts
(S-lec BX-1, manufactured by Sekisui Chemical Co., Ltd.)
Polyisocyanate curing agent 0.6 part
(Takenate D218, manufactured by Takeda Chemical Industries, Ltd.)
Phosphoric ester 0.8 part
(Plysurf A208, manufactured by Dai-Ichi Kogyo Seiyaku Co., Ltd.)
Methyl ethyl ketone (MEK) 42.5 parts
Toluene 42.5 parts <Preparation of Thermal Transfer Image Receiving Sheet 1>

A coating liquid, for adhesive layer formation, having the following composition was coated onto one surface of a 39 μm-thick microvoid film which is a microvoid layer, and the coated film was dried to form an adhesive layer. Subsequently, a support comprising a backside layer provided on one surface of a coated paper (186 g/m²) was laminated onto the microvoid film under forming conditions described later so that the adhesive layer faced the support on its surface remote from the backside layer of the support.

<Coating Liquid for Adhesive Layer Formation>
Polyfunctional polyol 30.0 parts
(Takelac A-969V, manufactured by Mitsui Chemicals, Inc.)
Isocyanate 10.0 parts
(Takenate A-5, manufactured by Mitsui Chemicals, Inc.)
Ethyl acetate 60.0 parts Subsequently, a coating liquid, for primer layer formation, having the following composition was coated by wire bar coating at a coverage of 2.0 g/m² on a dry basis on the microvoid film on its surface remote from the adhesive layer, followed by drying to form a primer layer.

<Coating Liquid for Primer Layer Formation>
Polyester polyol 15.0 parts
(Adcoat, Manufactured by Toyo-Morton, Ltd.)
Methyl ethyl ketone/toluene (mass ratio 2:1) 85.0 parts A coating liquid, for dye-receptive layer formation, having the following composition was coated by wire bar coating at a coverage of 4.0 g/m² on a dry basis on the primer layer, followed by drying to form a dye-receptive layer and thus to obtain a thermal transfer image receiving sheet 1.

<Coating Liquid for Dye-Receptive Layer Formation>
Vinyl chloride-vinyl acetate copolymer resin 20.0 parts
(Solbin C, manufactured by Nissin Chemical Industry CO., Ltd.)
(Vinyl chloride/vinyl acetate=87/13, number average molecular weight 31,000, glass transition temperature 70° C.)
Carboxyl-modified silicone 1.0 part
(X-22-3701E, manufactured by Shin-Etsu Chemical Co., Ltd.)
Methyl ethyl ketone/toluene (mass ratio 1:1) 79.0 parts <Preparation for Thermal Transfer Image Receiving Sheet 2>

A thermal transfer image receiving sheet 2 was obtained by providing a resin coat paper (STF-150, manufactured by Mitsubishi Paper Mills Ltd.) as a base material sheet, heating a coating liquid, for hollow layer A formation, having the following composition, a coating liquid, for hollow layer B formation, having the following composition, a coating liquid, for primer layer formation, having the following composition, and a coating liquid, for dye-receptive layer formation, having the following composition to 40° C., slid-coating the coating liquid for hollow layer A formation, the coating liquid for hollow layer B formation, the coating liquid for primer layer formation, and the coating liquid for dye-receptive layer formation in that order to respective thicknesses of 10 μm, 25 μm, 15 μm, and 13 μm on a wet basis on the base materila sheet, cooling the coatings at 5° C. for 30 sec, and drying the coatings at 50° C. for 2 min. The thermal transfer image receiving sheet 2 had a layer construction of base material/hollow layer A/hollow layer B/primer layer/dye-receptive layer stacked in that order.

<Coating Liquid for Hollow Layer a Formation>
Empty particles 60.0 parts
(average diameter 1 μm, average hollowness 50%)
(ROPAQUE HP-91, manufactured by Rohm & Haas)
Gelatin (RR, manufactured by Nitta Gelatin Inc.) 20.0 parts
MBR resin 20.0 parts
(Lacstar DM820, manufactured by DIC Corporation)
Surfactant 0.15 part
(Surfynol, manufactured by Nissin Chemical Industry CO., Ltd.)
Mater 400 parts <Coating Liquid for Hollow Layer B Formation
Empty particles 70.0 parts
(average diameter 1 μm, average hollowness 50%)
(ROPAQUE HP-91, manufactured by Rohm & Haas)
Gelatin (RR, manufactured by Nitta Gelatin Inc.) 25.0 parts
Polyester-urethane resin 5.0 parts
(Hydran AP-40, manufactured by DIC Corporation)
Surfactant 0.2 part
(Surfynol, manufactured by Nissin Chemical Industry CO., Ltd.)
Mater 500 parts <Coating Liquid for Primer Layer Formation>
Crosslinked empty particles 70.0 parts
(average diameter 0.3 μm, average hollowness 30%)
(SX-866, manufactured by JSR Corporation)
Gelatin (RR, manufactured by Nitta Gelatin Inc.) 25.0 parts
Acrylic resin 5.0 parts
(NKJ300, manufactured by Shin Nakamura Chemical Co., Ltd.)
Surfactant 0.2 part
(Surfynol, manufactured by Nissin Chemical Industry CO., Ltd.)
Water 500 parts <Coating Liquid for Dye-Receptive Layer Formation>
Vinyl chloride-acrylic copolymer resin 80.0 parts
(Vinyblan 900, manufactured by Nissin Chemical Industry CO., Ltd.)
Silicone release agent 10.0 parts
(KF-615A, manufactured by Nissin Chemical Industry CO., Ltd.)
Gelatin 20.0 parts
(G-0637K, manufactured by Nitta Gelatin Inc.)
Surfactant 0.5 part
(Surfynol, Manufactured by Nissin Chemical Industry Co., Ltd.)
Water 400 parts <Preparation of Printed Matter>

The thermal transfer image receiving sheets 1 and 2 were used as a transfer object. The thermal transfer image receiving sheet as the transfer object was put on a thermal transfer sheet comprising individual dye ribbons so that dye layers in the thermal transfer sheet faced the dye receiving surface in the transfer object, followed by thermal transfer recording with a thermal head from the back surface of the thermal transfer sheet to form a gradational image of black with printing energy at even intervals. After the image formation, an overcoating of a specialty ribbon for P-400 printer was thermally transferred. Printing conditions were as follows.

Printing Conditions
Thermal head: F3598 (manufactured by TOSHIBA HOKUTO
ELECTRONICS CORPORATION)
Average resistance of heating element: 5176 μl
Printing density in main scanning direction: 300 dpi
Printing density in feed direction: 300 dpi
Applied electric power: 0.12 W/dot
One line period: 2 msec
Pulse duty: 85%
Printing initiation temp.: 35.5 (° C.)

The black image thus obtained was irradiated with ultraviolet light for 96 hr (400 kJ) in a xenon weatherometer (manufactured by Atlas Material Testing Technology LLC, Ci4000: black panel temp. 45° C., filter: inside: CIRA, outside: soda lime, inside tester: 30° C., 30%, irradiation controlled ultraviolet light (420 nm) being fixed at 1.2 W/m$^2$), and the percentage change in density between before the irradiation and after the irradiation (density retention (%)=density after test/initial density×100) was determined. The density was confirmed by ΔE*ab around OD=1 before irradiation=((L* after irradiation−L* before irradiation)$^2$+(a* after irradiation−a* before irradiation)$^2$+(b* after irradiation−b* before irradiation)$^2$)$^{1/2}$ wherein L*, a* and b* are based on a CIE 1976 L*a*b* color system; L* represents lightness; and a* and b* represent a chromaticness index. Colorimetric conditions were as follows.

Colorimetric Conditions
Colorimeter: Spectrometer SpectroLino
(manufactured by Gretag Macbeth)
Light source: D65
View angle: 2°
Filter for density measurement: ANSI Status A The maximum sensitivity and lightfastness (ΔE*ab around OD=1 before irradiation) were as shown in Tables 5 to 8.

The dissolvability of each compound used in the preparation of magenta inks was evaluated according to the following criteria.

○: After the preparation of the ink, the coloring matter remained undissolved after standing at 10° C. for 24 hr.

Δ: After the preparation of the ink, the coloring matter remained dissolved after standing at 25° C. for 24 hr while crystals of the coloring matter were precipitated after standing at 10° C. for 24 hr.

x: After the precipitation of the ink, crystals of the coloring matter were precipitated after standing at 20° C. for 24 hr.

The results were as shown in Tables 5 to 8.

TABLE 5

| Combination of dye ribbons | | | Sensitivity | | Lightfastness | | |
|---|---|---|---|---|---|---|---|
| | | | Image receiving sheet 1 | Image receiving sheet 2 | Image receiving sheet 1 | Image receiving sheet 2 | |
| Yellow | Magenta | Cyan | | | | | Solubility |
| Ex. 1 | YE1 | MG1 | CY1 | 2.16 | 2.01 | 13 | 5 | ○ |
| Ex. 2 | YE1 | MG2 | CY1 | 2.20 | 2.03 | 12 | 5 | ○ |
| Ex. 3 | YE1 | MG3 | CY1 | 2.15 | 2.01 | 11 | 4 | ○ |
| Ex. 4 | YE1 | MG4 | CY1 | 2.19 | 2.03 | 12 | 4 | ○ |
| Ex. 5 | YE1 | MG5 | CY1 | 2.11 | 1.97 | 12 | 5 | ○ |
| Ex. 6 | YE1 | MG6 | CY1 | 2.21 | 2.04 | 12 | 5 | ○ |
| Ex. 7 | YE1 | MG7 | CY1 | 2.15 | 2.00 | 12 | 5 | ○ |
| Ex. 8 | YE1 | MG8 | CY1 | 2.16 | 2.00 | 13 | 5 | Δ |
| Ex. 9 | YE1 | MG9 | CY1 | 2.27 | 2.09 | 13 | 5 | ○ |
| Ex. 10 | YE1 | MG10 | CY1 | 2.29 | 2.11 | 13 | 5 | ○ |
| Ex. 11 | YE1 | MG13 | CY1 | 2.08 | 1.94 | 12 | 4 | ○ |
| Ex. 12 | YE1 | MG14 | CY1 | 2.00 | 1.87 | 11 | 4 | ○ |
| Comp. Ex. 1 | YE1 | MG11 | CY1 | 2.40 | 2.22 | 17 | 8 | ○ |
| Comp. Ex. 2 | YE1 | MG12 | CY1 | 1.57 | 1.40 | 16 | 6 | ○ |

TABLE 6

| Combination of dye ribbons | | | Sensitivity | | Lightfastness | | |
|---|---|---|---|---|---|---|---|
| | | | Image receiving sheet 1 | Image receiving sheet 2 | Image receiving sheet 1 | Image receiving sheet 2 | |
| Yellow | Magenta | Cyan | | | | | Solubility |
| Ex. 11 | YE2 | MG15 | CY2 | 1.94 | 1.81 | 15 | 5 | ○ |
| Ex. 12 | YE2 | MG16 | CY2 | 1.94 | 1.83 | 14 | 5 | ○ |
| Ex. 13 | YE2 | MG17 | CY2 | 1.89 | 1.80 | 13 | 4 | ○ |
| Ex. 14 | YE2 | MG18 | CY2 | 1.93 | 1.83 | 14 | 5 | ○ |
| Ex. 15 | YE2 | MG19 | CY2 | 1.87 | 1.80 | 14 | 5 | ○ |
| Ex. 16 | YE2 | MG20 | CY2 | 1.94 | 1.82 | 14 | 5 | ○ |
| Ex. 17 | YE2 | MG21 | CY2 | 1.90 | 1.81 | 14 | 5 | ○ |
| Ex. 18 | YE2 | MG22 | CY2 | 1.90 | 1.80 | 15 | 5 | Δ |
| Ex. 19 | YE2 | MG23 | CY2 | 1.99 | 1.86 | 15 | 5 | ○ |
| Ex. 20 | YE2 | MG24 | CY2 | 2.01 | 1.87 | 15 | 5 | ○ |
| Comp. Ex. 3 | YE2 | MG25 | CY2 | 2.10 | 1.92 | 19 | 9 | ○ |
| Comp. Ex. 4 | YE2 | MG26 | CY2 | 1.38 | 1.25 | 18 | 7 | ○ |

TABLE 7

| | Combination of dye ribbons | | | Sensitivity | | Lightfastness | | |
|---|---|---|---|---|---|---|---|---|
| | | | | Image receiving sheet 1 | Image receiving sheet 2 | Image receiving sheet 1 | Image receiving sheet 2 | |
| | Yellow | Magenta | Cyan | | | | | Solubility |
| Ex. 21 | YE3 | MG1 | CY1 | 1.94 | 1.81 | 15 | 6 | ○ |
| Ex. 22 | YE3 | MG3 | CY1 | 1.92 | 1.81 | 14 | 5 | ○ |
| Ex. 23 | YE3 | MG4 | CY1 | 1.96 | 1.83 | 14 | 5 | ○ |
| Ex. 24 | YE3 | MG6 | CY1 | 1.98 | 1.84 | 14 | 5 | ○ |
| Ex. 25 | YE3 | MG15 | CY2 | 1.87 | 1.80 | 14 | 6 | ○ |
| Ex. 26 | YE3 | MG17 | CY2 | 1.94 | 1.82 | 14 | 5 | ○ |
| Ex. 27 | YE3 | MG18 | CY2 | 1.90 | 1.81 | 15 | 4 | ○ |
| Ex. 28 | YE3 | MG20 | CY2 | 1.90 | 1.80 | 15 | 6 | ○ |
| Comp. Ex. 5 | YE3 | MG11 | CY1 | 2.11 | 1.98 | 19 | 9 | ○ |
| Comp. Ex. 6 | YE3 | MG25 | CY2 | 2.11 | 1.97 | 20 | 10 | ○ |

TABLE 8

| | Combination of dye ribbons | | | Sensitivity | | Lightfastness | | |
|---|---|---|---|---|---|---|---|---|
| | | | | Image receiving sheet 1 | Image receiving sheet 2 | Image receiving sheet 1 | Image receiving sheet 2 | |
| | Yellow | Magenta | Cyan | | | | | Solubility |
| Ex. 29 | YE1 | MG1 | CY3 | 2.15 | 2.01 | 13 | 5 | ○ |
| Ex. 30 | YE1 | MG3 | CY3 | 2.15 | 2.02 | 11 | 4 | ○ |
| Ex. 31 | YE1 | MG4 | CY3 | 2.19 | 2.03 | 12 | 4 | ○ |
| Ex. 32 | YE1 | MG6 | CY3 | 2.20 | 2.05 | 12 | 5 | ○ |
| Ex. 33 | YE1 | MG10 | CY3 | 2.27 | 2.12 | 13 | 5 | ○ |
| Ex. 34 | YE2 | MG15 | CY3 | 1.91 | 1.81 | 14 | 5 | ○ |
| Ex. 35 | YE2 | MG17 | CY3 | 1.90 | 1.81 | 13 | 4 | ○ |
| Ex. 36 | YE2 | MG18 | CY3 | 1.93 | 1.83 | 14 | 5 | ○ |
| Ex. 37 | YE2 | MG20 | CY3 | 1.95 | 1.83 | 14 | 5 | ○ |
| Ex. 38 | YE2 | MG24 | CY3 | 2.00 | 1.88 | 14 | 5 | ○ |
| Comp. Ex. 7 | YE1 | MG11 | CY3 | 2.38 | 2.21 | 17 | 8 | ○ |
| Comp. Ex. 8 | YE2 | MG25 | CY3 | 2.09 | 1.93 | 19 | 9 | ○ |

As is also apparent from the results shown in Tables 5 to 8, the thermal transfer sheets according to the present invention (Examples 1 to 38) were excellent in both density and lightfastness, whereas, for the thermal transfer sheets of Comparative Examples 1 to 8, thermal transfer sheets having excellent lightfastness had unsatisfactory density while thermal transfer sheets having excellent density had unsatisfactory lightfastness. When the thermal transfer sheets were applied to the thermal transfer image receiving sheet (transfer object 2) formed using the aqueous coating liquid for dye-receptive layer formation, further improved lightfastness was obtained as compared with the lightfastness in the application of the thermal transfer sheets to the thermal transfer image receiving sheet (transfer object 1) formed using the solvent-based coating liquid for dye-receptive layer formation.

The invention claimed is:

1. An azomethine compound represented by formula M-I:

[Chemical formula 1]

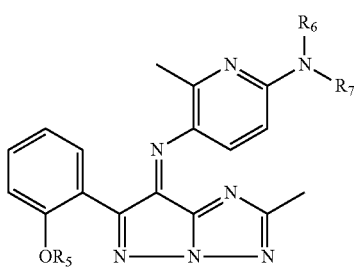

(M-I)

wherein
  $R_5$ represents a C1-3 (number of carbon atoms) straight chain or branched chain alkyl group; and
  $R_6$ and $R_7$ each independently represent a C2-4 (number of carbon atoms) alkyl group.

2. The azomethine compound according to claim 1, wherein $R_6$ and $R_7$ each represent a propyl or butyl group.

3. A process for producing an azomethine compound according to claim 1, the process comprising reacting a compound represented by formula II with a compound represented by formula III using an oxidizing agent in the presence of a base:

[Chemical formula 2]

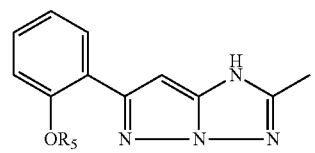

(II)

[Chemical formula 3]

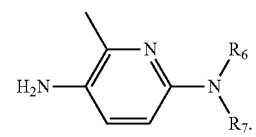

(III)

4. A coloring matter for thermal dye transfer recording, comprising an azomethine compound according to claim 1.

5. A thermal transfer sheet comprising at least a yellow dye layer, a magenta dye layer, and a cyan dye layer,
the yellow dye layer, the magenta dye layer, and the cyan dye layer each comprising a base material and a dye layer that contains a dye coloring matter and a binder resin and is provided on the base material, the magenta coloring matter being a coloring matter according to claim 4.

6. A thermal transfer sheet comprising at least a yellow dye layer, a magenta dye layer, and a cyan dye layer,
the yellow dye layer, the magenta dye layer, and the cyan dye layer each comprising a base material and a dye layer that contains a dye coloring matter and a binder resin and is provided on the base material,
the yellow dye comprising a dye coloring matter represented by formula Y-I and/or Y-II:

[Chemical formula 4]

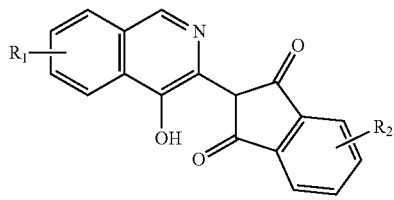

Y-I wherein $R_1$ represents an alkyl group, an aryl group, a hydrogen atom, or a halogen atom; and $R_2$ represents a carbonylamino group or a carbonylalkoxy group, and

[Chemical formula 5]

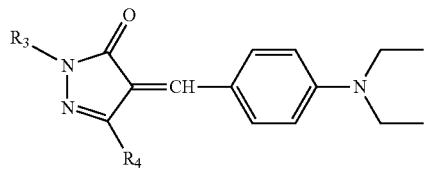

Y-II wherein $R_3$ represent an alkyl group, an aryl group, or a hydrogen atom; and $R_4$ represents an alkyloxyl group, an aryloxy group, or an amino group,
the magenta dye comprising a dye coloring matter represented by formula M-I:

[Chemical formula 6]

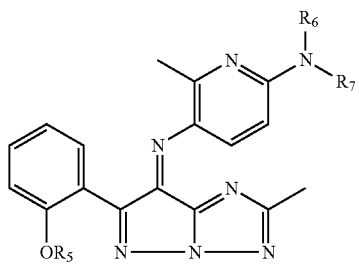

M-I wherein
$R_5$ represents a C1-3 (number of carbon atoms) straight chain or branched chain alkyl group; and
$R_6$ and $R_7$ each independently represent a C2-4 (number of carbon atoms) alkyl group,
the cyan dye comprising a dye coloring matter represented by formula C-I:

[Chemical formula 7]

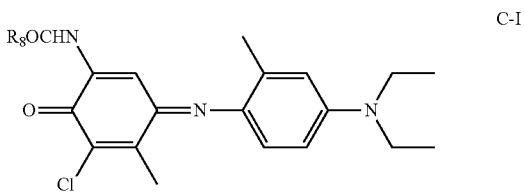

C-I wherein $R_8$ represents an alkyl group or an aryl group.

7. The thermal transfer sheet according to claim 6, wherein the dye coloring matter of formula Y-I is represented by formula Y-I-I, and the dye coloring matter of formula Y-II is represented by formula Y-II-I:

[Chemical formula 8]

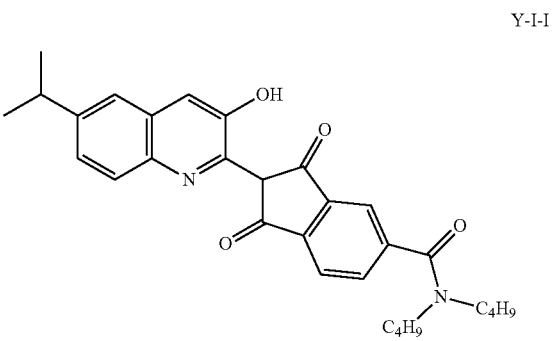

Y-I-I

[Chemical formula 9]

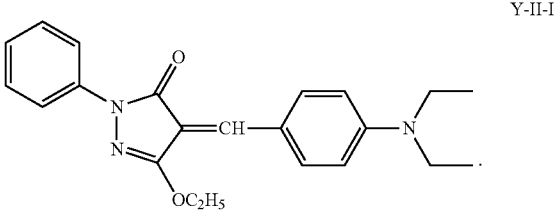

Y-II-I

8. The thermal transfer sheet according to claim 6, wherein the dye coloring matter of formula is represented by formula C-I-I:

[Chemical formula 10]

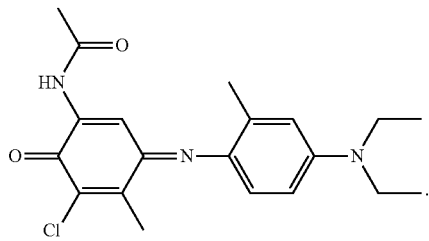

C-I-I

9. The thermal transfer sheet according to claim 6, wherein the magenta dye and the cyan dye further comprise a dye coloring matter represented by formula M-II:

[Chemical formula 11]

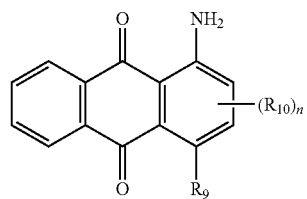

M-II wherein $R_9$ represents a substituted or unsubstituted alkoxycarbonyl group, a substituted or unsubstituted amino group, a hydroxy group, a substituted or unsubstituted alkoxy group, a substituted or unsubstituted aryloxy group, a substituted or unsubstituted alkyl group, a substituted or unsubstituted cycloalkyl group, a heterocyclic group, or a halogen atom; $R_{10}$ represents an amino group or a hydroxyl group; and n is integer of 2 or less, provided that, when a plurality of $R_{10}$s are present, $R_{10}$s may be the same or different.

10. The thermal transfer sheet according to claim 9, wherein the dye coloring matter of formula M-II is represented by formula M-II-I and/or formula M-II-II:

[Chemical formula 12]

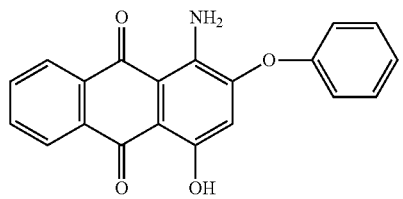

M-II-I

[Chemical formula 13]

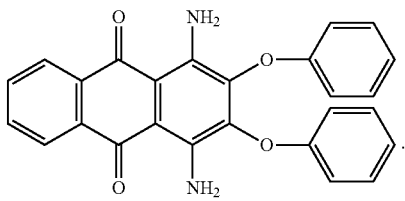

M-II-II

11. The thermal transfer sheet according to claim 6, wherein the yellow dye further comprises a dye coloring matter represented by formula Y-III and/or formula Y-IV:

[Chemical formula 14]

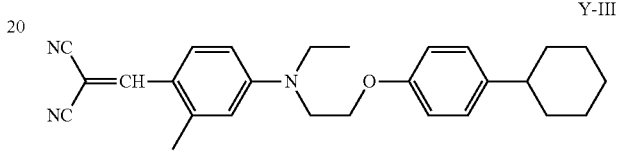

Y-III

[Chemical formula 15]

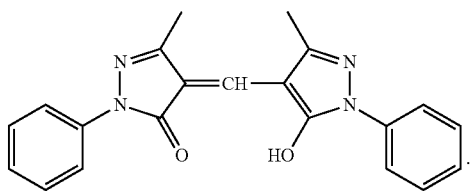

Y-IV

12. The thermal transfer sheet according to claim 6, wherein the cyan dye further comprises a dye coloring matter represented by formula C-II and/or formula C-III:

[Chemical formula 16]

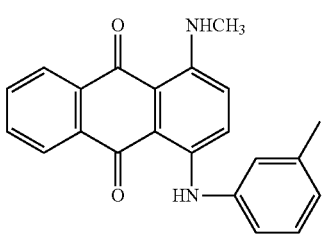

C-II

[Chemical formula 17]

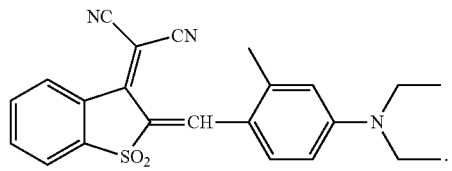

C-III

* * * * *